(12) United States Patent
Lawrence et al.

(10) Patent No.: US 9,244,034 B2
(45) Date of Patent: Jan. 26, 2016

(54) ELECTROCHEMICAL PH MEASUREMENT

(75) Inventors: Nathan S. Lawrence, Wyton (GB); Andrew Meredith, Cambridge (GB)

(73) Assignee: Schlumberger Technology Corporation, Sugar Land, TX (US)

( * ) Notice: Subject to any disclaimer, the term of this patent is extended or adjusted under 35 U.S.C. 154(b) by 639 days.

(21) Appl. No.: 13/464,700

(22) Filed: May 4, 2012

(65) Prior Publication Data
US 2012/0279874 A1    Nov. 8, 2012

Related U.S. Application Data

(63) Continuation-in-part of application No. PCT/GB2011/001509, filed on Oct. 20, 2011.

(60) Provisional application No. 61/410,145, filed on Nov. 4, 2010.

(30) Foreign Application Priority Data

Apr. 18, 2011    (GB) .................................. 1106498.7

(51) Int. Cl.
G01N 27/333    (2006.01)
G01N 27/30    (2006.01)
G01N 27/416    (2006.01)

(52) U.S. Cl.
CPC .............. *G01N 27/30* (2013.01); *G01N 27/302* (2013.01); *G01N 27/4167* (2013.01)

(58) Field of Classification Search
CPC .................................................. G01N 27/302
See application file for complete search history.

(56) References Cited

U.S. PATENT DOCUMENTS

| 3,780,575 A | 12/1973 | Urbanosky |
| 3,859,851 A | 1/1975 | Urbanosky |

(Continued)

FOREIGN PATENT DOCUMENTS

| GB | 2450002 | 12/2008 |
| GB | 2490117 | 10/2012 |

(Continued)

OTHER PUBLICATIONS

Shiu et al., "Potentiometric pH Sensor with Anthraquinonesulfonate Adsorbed on Glassy Carbon Electrodes," Electroanalysis 1996, 8, No. 12, pp. 1160-1164.*

(Continued)

*Primary Examiner* — Alexander Noguerola

(57) ABSTRACT

A method of measuring pH of aqueous liquid with little or no buffer present uses an electrochemical pH sensor which comprises a plurality of electrodes with a redox active organic compound attached to an electrode and having at least one functional group convertible electrochemically between reduced and oxidized forms with transfer of at least one proton between the compound and surrounding aqueous phase, wherein the compound has at least one substituent group which promotes hydrogen bonding at a said functional group and thereby increases the reaction rate of proton transfer. The substituent group may form an internal hydrogen bond with a redox-convertible group or may enhance polarity to promote electrostatic interaction with water molecules and reduce activation energy. Such an electrochemical sensor may be used for pH measurement in computer controlled equipment for processing an aqueous liquid.

11 Claims, 12 Drawing Sheets

(56) References Cited

U.S. PATENT DOCUMENTS

| | | | |
|---|---|---|---|
| 4,994,671 | A | 2/1991 | Safinya et al. |
| 5,133,856 | A | 7/1992 | Yamaguchi et al. |
| 5,139,626 | A | 8/1992 | Yamaguchi et al. |
| 5,223,117 | A | 6/1993 | Wrighton et al. |
| 5,676,820 | A | 10/1997 | Wang et al. |
| 5,736,650 | A | 4/1998 | Hiron et al. |
| 5,829,520 | A | 11/1998 | Johnson |
| 6,451,603 | B1 | 9/2002 | Atkins et al. |
| 7,600,419 | B2 | 10/2009 | Oddie |
| 7,707,898 | B2 | 5/2010 | Oddie |
| 2001/0032785 | A1 | 10/2001 | Cha et al. |
| 2008/0023328 | A1 | 1/2008 | Jiang et al. |
| 2010/0016699 | A1 | 1/2010 | Wadhawan et al. |
| 2011/0048969 | A1 | 3/2011 | Lawrence et al. |
| 2012/0279874 | A1 | 11/2012 | Lawrence et al. |

FOREIGN PATENT DOCUMENTS

| | | | | |
|---|---|---|---|---|
| JP | 55-109956 A | * | 8/1980 | ............ G01N 27/46 |
| JP | 61155949 | | 7/1986 | |
| JP | 61194343 | | 8/1986 | |
| JP | 61213660 | | 9/1986 | |
| JP | 61213662 | | 9/1986 | |
| JP | 61251764 | | 11/1986 | |
| WO | WO 98-11426 A1 | * | 3/1998 | ............ G01N 27/40 |
| WO | 2005066618 | | 7/2005 | |
| WO | 2007034131 | | 3/2007 | |
| WO | 2010001082 | | 1/2010 | |
| WO | 2010106404 | | 9/2010 | |
| WO | 2010111531 | | 9/2010 | |
| WO | 2012059708 | | 5/2012 | |

OTHER PUBLICATIONS

Sigma-Aldrich product specification for Anthraquinone-2-sulfonic acid sodium salt monohydrate—97%, publication date not indicated.*

Reza et al., A Cyclic Voltammetric Study of the Aqueous Electrochemistry of Some Anthraquinone Derivatives on Carbon Paste Electrodes, Iran J. Chem. & Chem. Eng. vol. 20, No. 2, pp. 75-81, 2001.*

Philip Elving, "Variation of the Half-Wave Potential of Organic Compounds with pH," Pure and Applied Chemistry, vol. 7, issue 2-3 (Jul. 1963), pp. 423-454.*

Derwent abstract of Hamamoto et al. JP 55-109956 A, patent published Aug. 23, 1980.*

Combined Search and Examination Report of British Application No. GB1106498.7 (IS11.0199 GB) dated Jul. 22, 2011: pp. 1-6.

International Search Report of PCT Application No. PCT/GB2011/001509 dated Feb. 22, 2012: pp. 1-5.

Extended Search Report of European Application No. 12166704.2 dated Oct. 26, 2012: pp. 1-10.

Bailey et al., "A Cyclic Voltammetric Study of the Aqueous Electrochemistry of Some Quinones," Electrochimica Acta, 1985, vol. 30(1): pp. 3-12.

Bard et al., "Chapter 6: Potential Sweep Methods," "Chapter 7: Pulse Voltammetry," "Chapter 7.3.5: Square Wave Voltammetry" and "Chapter 15.4: Potentiostats," Electrochemical Methods Fundamentals and Applications, Second Edition, John Wiley & Sons: New York, 2001: pp. 226-252, 275, 293-301 and 640-644.

Batchelor-McAuley et al., "Voltammetric Responses of Surface-Bound and Solution-Phase Anthraquinone Moieties in the Presence of Unbuffered Aqueous Media," J. Phys. Chem. C, 2011, vol. 115: pp. 714-718.

Downard et al., "Voltammetric determination of aluminium (III) using a chemically modified electrode," Analytica Chimica Acta, 1991, vol. 251: pp. 157-163.

Forster, "Kinetic Separation of Amperometric Sensor Responses," Analyst, Jun. 1996, vol. 121: pp. 733-741.

Forster, "Coupled Proton and Electron Transfer: Adsorbed Anthraquinone-2-carboxylic Acid Monolayers," J. Electrochem. Soc., Apr. 1997, vol. 144(4): pp. 1165-1173.

Forster et al., "Protonation reactions of anthraquinone-2, 7-disulphonic acid in solution and within monolayers," Journal of Electroanalytical Chemistry, 2001, vol. 498: pp. 127-135.

O'Hanlon et al., "Intermolecular Hydrogen Bonding: Two-Component Anthraquinone Monolayers," Langmuir, 2000, vol. 16: pp. 702-707.

Park et al., "In-Situ ESR Detection of Radical Species of p-Benzoquinone in Aqueous Media," Electroanalysis, 2002, vol. 14(21): pp. 1501-1507.

Quan et al., "Voltammetry of Quinones in Unbuffered Aqueous Solution: Reassessing the Roles of Proton Transfer and Hydrogen Bonding in the Aqueous Electrochemistry of Quinones," J. Am. Chem. Soc., 2007, vol. 129: pp. 12847-12856.

Robertson et al., "Microelectrodes as probes in low electrolyte solutions: the reduction of quinone in aqueous sulfuric acid solution," Journal of Electroanalysis Chemistry, 1994, vol. 374: pp. 173-177.

Rubinstein, "Voltammetric pH Measurements with Surface-Modified Electrodes and a Voltammetric Internal Reference," Anal. Chem., 1984, vol. 56: pp. 1135-1137.

Scholz et al., "Voltammetry of Solid Microparticles Immobilized on Electrode Surfaces," Electroanalytical Chemistry A Series of Advances, vol. 20, eds.: Bard et al., Marcel Dekker, Inc.: New York, 1998: pp. 1-86.

Zinger, "Electrochemistry of Quinizarine Adsorbed on a Glassy Carbon Electrode in Aqueous Solutions," J. Electroanal. Chem., 1988, vol. 239: pp. 209-225.

Batchelor-McAuley et al., "Voltammetry of Multi-electron Electrode Processes of Organic Species," Journal of Electroanalytical Chemistry, 2012, vol. 669: pp. 73-81.

Bhattacharyya et al., "Combined Quantum Mechanical and Molecular Mechanical Simulations of One- and Two-Electron Reduction Potentials of Flavin Cofactor in Water, Medium-Chain Acyl-CoA Dehydrogenase, and Cholesterol Oxidase," J. Phys. Chem. A, 2007, vol. 111: pp. 5729-5742.

Comninellis et al., "Electrochemical Oxidation of Phenol for Wastewater Treatment Using SnO2 Anodes," Journal of Applied Electrochemistry, 1993, vol. 23: pp. 108-112.

Comninellis et al., "Anodic Oxidation of Phenol in the Presence of NaCl for Wastewater Treatment," Journal of Applied Electrochemistry, 1995, vol. 25: pp. 23-28.

Enache et al., "Phenol and Para-Substituted Phenols Electrochemical Oxidation Pathways," Journal of Electroanalytical Chemistry, 2011, vol. 655: pp. 9-16.

Ghanem, "Electrocatalytic Activity and Simultaneous Determination of Catechol and Hydroquinone at Mesoporous Platinum Electrode," Electrochemistry Communications 9, 2007: pp. 2501-2506.

Kipp, "PHCALC: A Computer Program for Acid/base Equilibrium Calculations," Computer Series 158, Feb. 1994, vol. 71(2): pp. 119-121.

Stradins et al., "Anodic Voltammetry of Phenol and Benzenethiol derivatives. Part 1. Influence of pH on Electro-Oxidation Potentials of Substituted Phenols and Evaluation of pKa from Anodic Voltammetry data", J. Electroanal. Chem., 1993, vol. 353: pp. 57-69.

* cited by examiner

ELECTROCHEMICAL PH MEASUREMENT

CROSS-REFERENCE TO RELATED APPLICATIONS

This application claims priority to and is a continuation-in-part of International Patent Cooperation Treaty Patent Application No. PCT/GB2011/001509 filed Oct. 20, 2011, and entitled, "Electrochemical Sensor," which claims benefit of U.S. Provisional Patent Application Ser. No. 61/410,145 filed Nov. 4, 2010, and entitled, "Electrochemical Sensor." Both of these applications are incorporated by reference herein.

BACKGROUND OF THE INVENTION

There are numerous circumstances in which it is desirable to detect, measure or monitor a constituent of a fluid. One of the commonest requirements is to determine hydrogen ion concentration (generally expressed on the logarithmic pH scale) in aqueous fluids which may for example be a water supply, a composition in the course of production or an effluent. The determination of the pH of a solution is one of the most common analytical measurements and can be regarded as the most critical parameter in water chemistry. Merely by way of example, pH measurement is important in the pharmaceutical industry, the food and beverage industry, the treatment and management of water and waste, chemical and biological research, hydrocarbon production and water supply monitoring. Nearly all water samples will have their pH tested at some stage during their handling as many chemical processes are dependent on pH.

It may also be desired to measure pH of a fluid downhole in a wellbore. The concentrations of some chemical species, such as $H^+$ and $H_2S$ may change significantly while tripping to the surface. The change occurs mainly due to a difference in temperature and pressure between downhole and surface environment. In case of samples taken downhole, this change may also happen due to degassing of a sample (seal failure), mineral precipitation in a sampling bottle, and chemical reaction with the sampling chamber. The value of pH is among the parameters for corrosion and scale assessment. Consequently it is of considerable importance to determine pH downhole.

One approach to pH measurements, both at the Earth's surface and downhole, employs a solid-state probe utilising redox chemistries at the surface of an electrode. Some redox active compounds (sometimes referred to as redox active species) display a redox potential which is dependent on hydrogen ion concentration in the electrolyte. By monitoring this redox potential electrochemically, pH can be determined. Voltammetry has been used as a desirable and convenient electrochemical method for monitoring the oxidation and reduction of a redox active species and it is known to immobilise the redox active species on or in proximity to an electrode.

Prior literature in this field has included WO2005/066618 which disclosed a sensor in which two different pH sensitive molecular redox systems and a pH insensitive ferrocene reference were attached to the same substrate. One pH sensitive redox system was anthraquinone (AQ) and the second was either phenanthrenequinone (PAQ) or alternatively was N,N'-diphenyl-p-phenylenediamine (DPPD). WO2007/034131 disclosed a sensor with two redox systems incorporated into a copolymer. WO2010/001082 disclosed a sensor in which two different pH sensitive molecular redox systems were incorporated into a single small molecule which was immobilized on an electrode. WO2010/111531 described a pH metering device using a working electrode in which a material which is sensitive to hydrogen ions (the analyte) was chemically coupled to carbon and immobilised on the working electrode.

An issue with electrochemical sensors (particularly those involving detection mechanisms involving proton transfer) is the ability to make electrochemical measurements without a buffer and/or similar species that can facilitate proton transfer reactions. Measurements can be particularly difficult, and error prone, in low ionic strength media, without pH buffering species and/or other species facilitating proton transfers. Measuring the pH of rainwater, and natural waters with very low mineralization, is noted as being particularly difficult.

Merely by way of example, in water industries, such as the management of reservoirs and waste management, the samples being tested or the reservoirs being monitored may not include a buffer solution or the like. Even in non-water industries, there may be occasions when the samples being tested or the fluid being monitored have low amounts of "natural buffers".

A pH sensor is often tested and calibrated using buffer solutions which have stable values of pH. The concentration of buffer in such a solution may be 0.1 molar or more. It has been discovered that electrochemical sensors utilising an immobilized redox compound can give good results when used in a buffered aqueous solution, and yet fail to do so when used in an unbuffered solution. A number of authors have appreciated this and it has been proposed that the electrochemistry of quinones in unbuffered, near neutral solution differs from that observed in buffered or strongly acid solution. See for example Quan et al., J. Am. Chem. Soc. Vol. 129, pages 12847 to 12856 (2007). Quan et al. argue that a different mechanism becomes operative in aqueous solution when proton concentration becomes low. Batchelor-McAuley et al., J. Phys. Chem. C Vol. 115, pages 714-718 (2011) attribute the different behaviour in unbuffered solution to depletion of $H^+$ ion concentration in the vicinity of the electrode resulting in a significant local change in pH adjacent to the electrode and thus an erroneous determination of pH within the bulk solution. In unpublished work we have tried to overcome this by use of a rotating electrode to change the mass transport regime in the vicinity of the electrode, but without appreciable success.

SUMMARY

We have found that anomalous values of pH can be obtained from an electrochemical sensor when there is no buffer and also when buffer is present in the electrolyte at low concentration. However, this difficulty in measurement can be significantly mitigated through choice of substituents on the redox active compound which is used.

In one aspect, the present disclosure provides a method of measuring the pH of water or another aqueous liquid, which may possibly contain buffer at a concentration up to 0.01 Molar (i.e., does not exceed 10 milliMolar), comprising exposing the water or other aqueous liquid to an electrochemical sensor which comprises an electrode with a redox active compound immobilized to the electrode and having at least one functional group convertible electrochemically between reduced and oxidized forms with transfer of at least one proton between the compound and surrounding aqueous liquid, wherein the compound has at least one substituent group which increases the reaction rate of proton transfer by reducing the activation energy for transfer of a proton and/or promoting hydrogen bonding at a said functional group.

The method may comprise observing the redox reaction at the electrochemical sensor. More specifically, the method may comprise applying variable potential to the electrode with the redox-active compound immobilized thereon and determining the applied potential at a maximum current for redox reaction of the compound.

This disclosure also includes apparatus for carrying out the method, comprising an electrochemical sensor as defined above. The electrochemical sensor may possibly be positioned to carry out measurement on flowing liquid, such as liquid flowing in a process plant, or on samples which are automatically and repeatedly taken from a flowing liquid.

Concentration of buffer is the total concentration of partially dissociated acid, base and/or salt which provides the stabilisation of pH. The method and/or the use of a sensor may be carried out to measure the pH of an aqueous liquid which contains buffer at a concentration of at least $10^{-6}$ molar (0.001 mM) or possibly at least $5 \times 10^{-6}$ molar (0.005 mM), or at least $10^{-5}$ molar or at least $10^{-4}$ molar. The concentration of buffer may perhaps be no more than $5 \times 10^{-3}$ molar (5 mM) or even no more than 1 mM.

Because measurement can be made when buffer is at a low concentration, measurement can be performed on aqueous liquids where a small concentration of buffer may be present as a consequence of the origin of the liquid, for example measurement may be carried out on biological samples and natural products containing small concentrations of organic acids which are not fully ionised and provide some buffering of pH.

It is envisaged that the aqueous liquid may have a pH which is within two or three units of neutral. Thus the liquid may be mildly acidic from pH 4 or pH 5 up to pH 7 or mildly basic from pH 7 up to pH 9 or pH 10. The aqueous liquid may be liquid flowing within or sampled from equipment for processing the liquid and it may be a foodstuff or other material for human or animal consumption or an ingredient of such foodstuff or material. The aqueous liquid may be one phase of a composition which is an emulsion, and it may be the continuous phase or a discontinuous phase of an emulsion.

Measurement of pH by the stated method can be carried out without measuring the buffer concentration. It is advantageous that the method can be employed when buffer concentration in the aqueous liquid is not known or is a parameter which cannot be controlled, without fear of an anomalous result because the concentration of buffer is low.

In a further aspect, the present disclosure provides apparatus to determine pH of water or other aqueous solution. Such apparatus may comprise an electrochemical sensor comprising a redox active compound immobilized to an electrode and having at least one functional group convertible electrochemically between reduced and oxidized forms with transfer of at least one proton between the compound and surrounding aqueous phase, means to apply potential to the electrode and observe current flow, and a programmable computer connected and configured to receive current and/or voltage data from the sensor, wherein (as already mentioned above) the redox active compound has at least one substituent group which increases the reaction rate of proton transfer by reducing the activation energy for transfer of a proton and/or promoting hydrogen bonding at a said functional group.

Such apparatus may be incorporated as equipment to process aqueous liquid, for instance process plant for water treatment, or to manufacture a pharmaceutical or a food product, and the computer which receives data from the sensor may be a computer which monitors or controls operation of that equipment. Thus this disclosure also provides equipment for processing water or other aqueous liquid, including:

a programmable computer operatively connected to control or monitor operation of the equipment, an electrochemical sensor comprising a redox active compound immobilized to an electrode and having at least one functional group convertible electrochemically between reduced and oxidized forms with transfer of at least one proton between the compound and surrounding aqueous phase, wherein the redox active compound has at least one substituent group which increases the reaction rate of proton transfer by reducing the activation energy for transfer of a proton and/or promoting hydrogen bonding at a said functional group, and means to apply potential to the electrode and observe current flow; wherein the computer is connected and configured to receive current and/or voltage data from the sensor.

The electrochemical sensor may be positioned in the equipment to be exposed to liquid flowing within the equipment, or taken from it as a sample, possibly by automated sampling under control of the computer. A programmable computer may monitor the proper operation of equipment and give a readout to a human operator, or the computer may itself control operation of the equipment.

The liquid whose pH is measured by such apparatus and equipment may be unbuffered, or may contain buffer in a concentration up to or above 0.1 molar. Incorporating an electrochemical sensor as defined mitigates the risk of anomalous determinations of pH in the event that the buffer concentration is low.

It is envisaged that the redox active compound which is carried on or in the sensor will be insoluble in water. It may be immobilised on the surface of an electrode or held within a porous electrode, such as a screen printed or carbon paste electrode.

One possibility for a substituent group to promote hydrogen bonding is a group containing oxygen or nitrogen and positioned to participate in hydrogen bonding with a water molecule also able to hydrogen bond to the redox active functional group. More specifically, this substituent may be a hydroxyl group. Another possibility is a group containing a hetero atom (which is neither carbon nor hydrogen) which increases the polarity of the molecule and electrostatic interaction with water molecules in the electrolyte. Such a group may be an electron withdrawing group positioned to be able to withdraw electrons from the redox active functional group. Without limitation as to mode of action, we believe that these possibilities promote hydrogen bonding between the redox active functional group and an adjacent water molecule and this is believed to reduce the activation energy for proton transfer and so increase the reaction rate of proton transfer.

Again, without limitation as to theory, we believe that by facilitating proton transfer from the electrode to the solution the mechanism changes from a non-concerted electron, proton transfer towards a concerted process in which the electrons and protons are exchanged simultaneously, or practically simultaneously on the timescales of the measurement through fast electron-proton transfers. So the redox active organic compound may have a structure such that the electron and proton transfer are concerted when there is electrochemical conversion between its reduced and oxidized forms.

Aromatic compounds which have two groups convertible between a reduced hydroxyl form and an oxidised keto form by a two electron, two proton reaction have been previously been found to be particularly suitable as pH sensitive redox active species: anthraquinone is a common example. A compound of this character may be used, with structure and substituent groups which promote hydrogen bonding at the hydroxyl/keto functional groups and thereby increase the reaction rate of proton transfer. The redox active organic compound may comprise at least two fused aromatic rings with oxygen or nitrogen-containing substituents, convertible between reduced and oxidised forms, on adjacent fused aromatic rings in positions allowing formation of an internal hydrogen bond between the reduced form of one said substituent and the oxidised form of another said substituent.

A number of redox active compounds which are suitable have an oxidation potential greater than 0.4 Volts with respect to a saturated calomel electrode, when measured in a pH 1.7 solution.

Embodiments of electrochemical sensor may have a plurality of electrodes with the redox active aromatic organic compound immobilized on one of the electrodes. An electrochemical sensor may comprise a second redox active compound as a reference, immobilized to the same or another electrode, where the oxidation and reduction of the reference redox active compound is substantially insensitive to pH. An electrochemical sensor may form part of apparatus for measuring pH in which means to apply potential to the electrode and observe current flow comprises means for applying varying potential to the sensor and observing one or more oxidation and reduction potentials to determine pH. Measuring pH may comprise applying a potential to the sensor in a sweep over a range sufficient to bring about at least one oxidation and/or reduction of the redox active compound; measuring potential or potentials at the peak current for one or more said oxidation and/or reductions; and processing the measurements to give a determination of pH. If more than one potential is measured, the method may comprise averaging at least two potentials corresponding to peak currents and processing the average to determine the pH.

DETAILED DESCRIPTION

Figure 1:
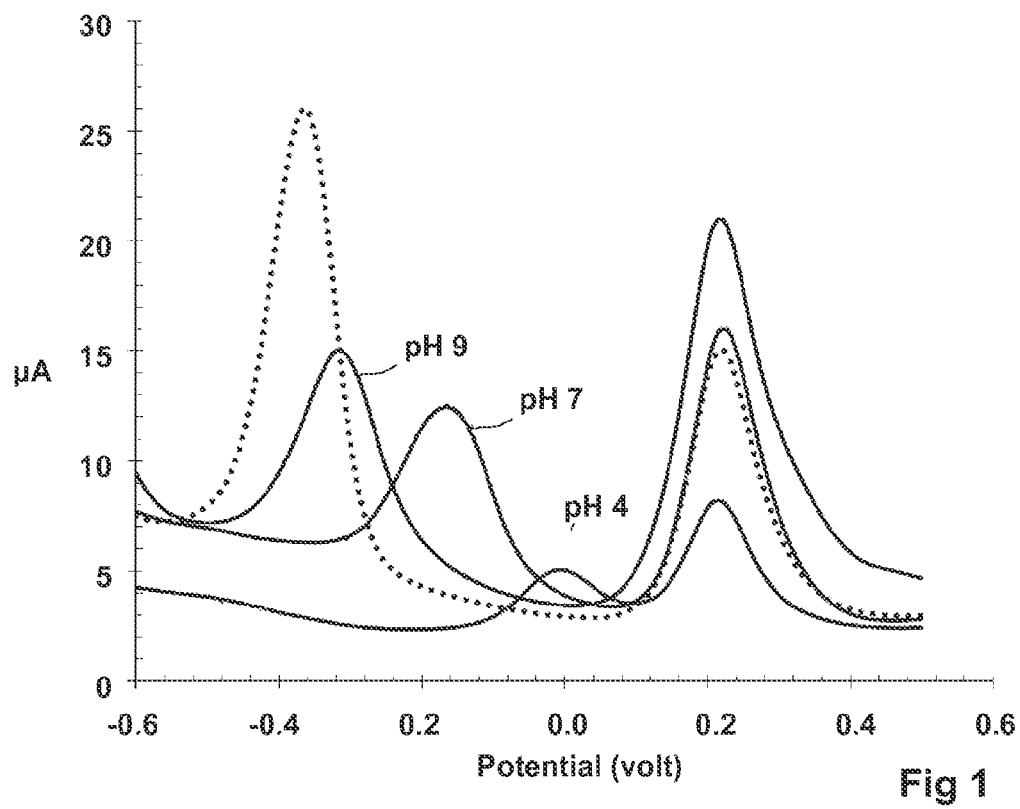
FIG. 1 shows the result of square wave voltammetry of PAQ in buffered and unbuffered solutions, and is discussed in Comparative Example 1.

The following so called "scheme of squares" for the two electron two proton redox conversion of anthraquinone (AQ) to and from anthrahydroquinone which is its corresponding reduced form shows that the reaction can proceed through a number of intermediates which are unstable in water:

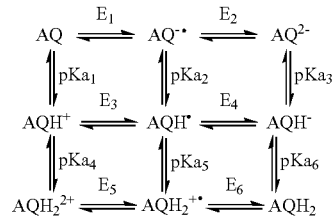

This reaction scheme is the accepted mechanism in aqueous buffered media.

If the electrochemical reaction is examined by cyclic voltammetry, the response shows oxidative peak and reductive peak currents at different voltages (more strictly, at different applied potentials relative to a reference electrode). The voltage at the oxidative current peak is higher than the voltage at the reductive current peak. The theory of voltammetry and its application to measurements are both well developed. The subject is discussed in WO 2005/066618 above and is covered in standard textbooks, such as A J Bard and L Faulkner, "Electrochemical Methods: Fundamentals and Applications" ($2^{nd}$ ed 2001).

In a buffered solution with a buffer concentration such as 0.1 molar or more, the voltages at which the oxidative peak current and reductive peak current occur are linearly dependent on pH and a straight line plot of peak current voltage against pH can be obtained by determining peak current voltages in a number of buffer solutions of known pH. Because the voltages of the oxidative peak current and reductive peak current are both linearly dependent on pH, a straight line through data points can be obtained by plotting voltages at either oxidative peak current or reductive peak current against pH. A straight line scan also be obtained by plotting the mean of these two voltages against pH. With all three of these possibilities the resulting straight line plot can then serve as calibration for determining pH of other aqueous liquids.

This dependence of voltage at peak current on pH is a general phenomenon observed with quinones and other compounds which undergo two electron two proton redox reactions, and also with compounds which undergo one electron one proton reactions.

As already mentioned, it has been observed that data points obtained with simple quinones in unbuffered solutions do not lie on the straight line through the points obtained in buffer solutions and so indicate an anomalous value of pH. As shown by comparative examples below, anomalous values of pH are also obtained when the electrolyte contains buffer at low concentration. The inventors have now discovered that some redox active compounds, when immobilised on an electrode, considerably reduce these anomalies so that a more reliable determination of pH is made.

In embodiments, the compounds have structures and substituents which enhance hydrogen bonding to the water which is in contact with the electrode.

In one category of compounds the hydrogen bonding is enhanced by structure which allows the formation of an internal hydrogen bond with the group which is redox active. This may be an internal hydrogen bond between an appropriately positioned keto group and a hydroxy group capable of oxidation to a keto group. Such an internal hydrogen bond assists in the formation of an external hydrogen bond with an adjacent water molecule which in turn reduces the activation energy for proton transfer. A number of structures are possible. The structure may incorporate a partial structure which is

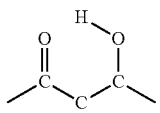

where the three carbon atoms are joined by conjugated bonds with delocalised electrons. Such a structure could be provided by an acetyl substituent on an aromatic ring, adjacent to a hydroxyl or keto group, as for example in 2-acetyl hydroquinone. However, all three carbon atoms may be in a fused aromatic ring structure which may be depicted as

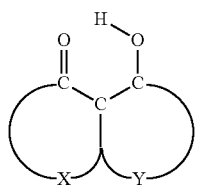

where X and Y denote the remainder of fused aromatic rings. These rings may bear substituents and may be fused with further aromatic or aliphatic rings.

In some embodiments the rings each have two redox active oxygen-containing substituents so that they are convertible between dihydroxy and diketo forms. Possibly, only one of the two oxygen-containing substituent on each ring is positioned to form an internal hydrogen bond and this may accelerate the first proton transfer of a two electron two proton redox reaction. An example of such a compound is 1,2-dihydroxyanthraquinone (1,2-DHAQ) which has the formula

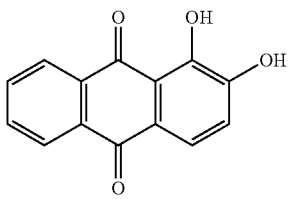 [SMILES: O=C1c2ccccc2C(=O)c2c1ccc(O)c2O]

In another category of compounds, hydrogen bonding to adjacent water molecules is enhanced by electron withdrawing substituents which may be halogen atoms. A compound may have one, preferably two oxygen containing substituents on an aromatic ring and a number of electron withdrawing substituents on that ring or connected to that ring through conjugated bonds, as is the case with substituents on one or more further aromatic rings which are fused with the first ring.

An example compound with two oxygen containing substituents and four electron withdrawing groups is tetra bromo catechol which has the formula

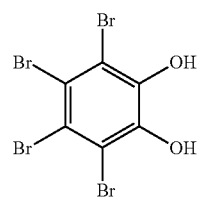 [SMILES: Oc1c(O)c(Br)c(Br)c(Br)c1Br]

A number of examples will now be set out, demonstrating the anomaly in pH determinations and the reduction or avoidance of anomalous pH determinations. These examples all used the same procedure for immobilising redox compounds on an electrode and used similar procedures for carrying out voltammetric measurements. In these examples a water-insoluble redox compound to be examined was dissolved at a concentration of 1 mg/ml in dichloromethane. 10 microliter of this solution was applied to the surface of a glassy carbon electrode and allowed to evaporate, thus depositing the redox compound on the electrode surface.

Such an electrode was then used for the voltammetric measurement of the electromotive force (e.m.f.) or potential E in a potentiometric cell. The cell was also equipped with a platinum wire counter electrode and a saturated calomel reference electrode. A potentiostat was used to carry out square wave voltammetry, measuring and recording the current which flows as the applied voltage is varied. Suitable potentiostats are available from Eco Chemie BV, Utrecht, Netherlands.

The electrodes with redox compounds deposited on them were used for voltammetry. The voltages (i.e., applied potentials) at which the oxidative and reductive currents reached their maxima were recorded as the voltage differences from the reference electrode.

Comparative Example 1

Figure 2:
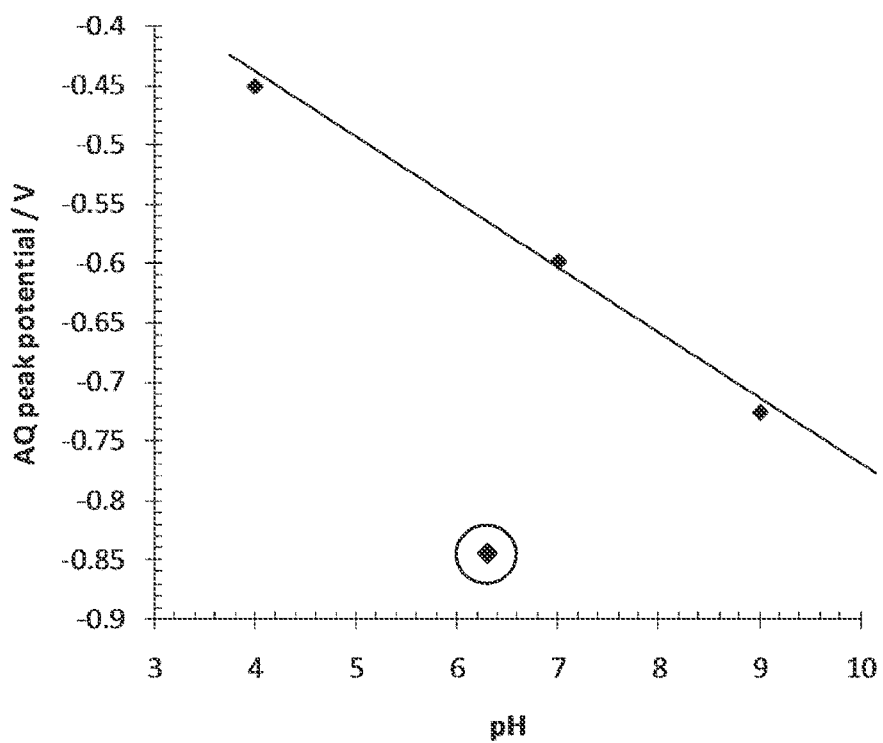
FIG. 2 shows voltages at the current peaks in FIG. 1 plotted against pH.
Figure 3:
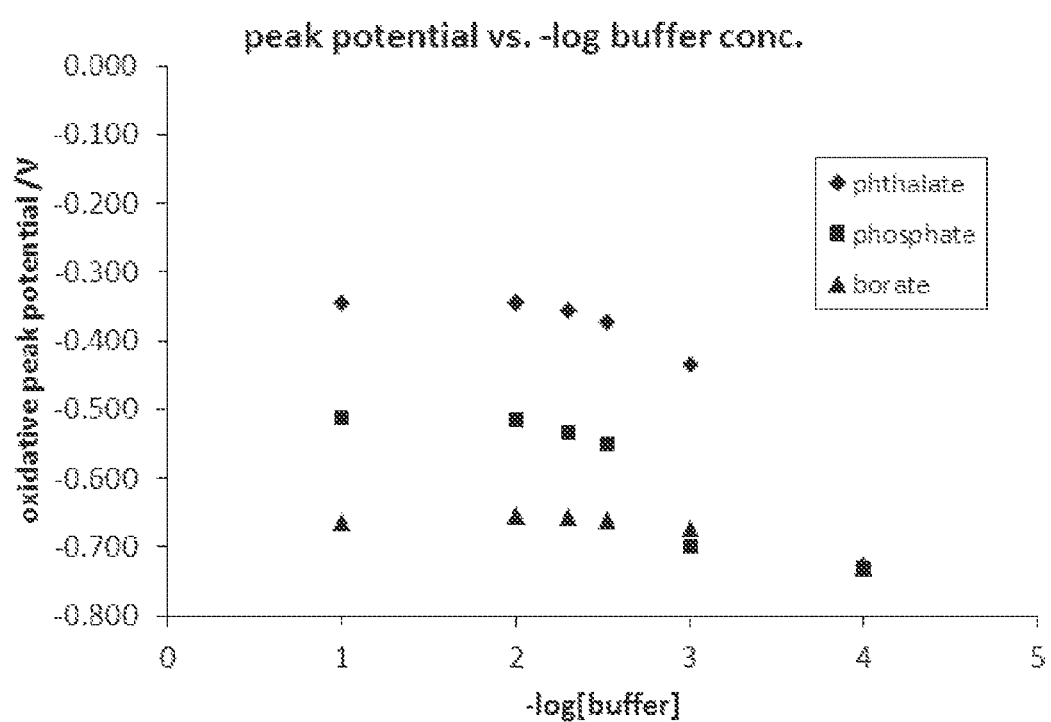
FIG. 3 shows voltages at current peaks obtained in Comparative Example 2 plotted against minus log buffer concentration.

For this example the test electrode had phenanthraquinone (PAQ) deposited on it in the manner described above. A pH insensitive electrode was prepared in the same way, using ferrocene as the redox compound. This electrode and the test electrode were electrically connected. FIG. 1 shows as continuous curves the oxidative responses obtained by square wave voltammetry in standard buffer solutions of 0.1 molar concentration and having pH 4, pH 7 and pH 9 as electrolyte. The voltages at oxidative peak currents were plotted against pH as shown as FIG. 2. The data points obtained in buffer solutions lie on an obvious straight line which serves as a calibration for measuring the pH of other solutions.

FIG. 1 also shows (as a dotted line) the voltammetric response when the electrolyte was unbuffered 0.1 molar sodium chloride solution at pH 7. The oxidative peak current was at an anomalous low voltage, erroneously indicating a pH above 10. This anomalous data point is shown circled in FIG. 2. This anomaly is also observed with anthraquinone (AQ).

Comparative Example 2

For this example the test electrode had anthraquinone (AQ) deposited on it in the manner described above. Voltammetry was carried out in aqueous solutions containing buffer at low concentration. Three buffers were used:

a phosphate buffer contained $Na_2HPO_4$ and $KH_2PO_4$ in proportions to buffer the solution to pH7.0 as determined using a glass electrode. The molar concentration of buffer was the total molar concentration of all phosphate ions;

a phthalate buffer contained potassium hydrogen phthalate with pH adjusted by addition of hydrochloric acid to pH4.0 as determined using a glass electrode. Buffer concentration was the total concentration of phthalate; and a borate buffer contained boric acid and sodium tetraborate in proportions to buffer at pH9.0 as determined using a glass electrode. Buffer concentration was the total molar concentration of all borate ions.

Square wave voltammetry was carried out in solutions containing these buffers at a variety of concentrations ranging from 0.0001 molar to 0.1 molar, together with potassium chloride where required to make up the electrolyte concentration to 0.1 Molar. The voltages corresponding to peak oxidative current were measured, and the results are set out in the following table.

| Buffer(molar) | minus log Buffer conc. | phthalate | phosphate | borate |
|---|---|---|---|---|
| 0.1 | 1 | −0.34 | −0.51 | −0.66 |
| 0.01 | 2 | −0.35 | −0.52 | −0.66 |
| 0.005 | 2.30 | −0.36 | −0.53 | −0.66 |
| 0.003 | 2.52 | −0.37 | −0.55 | −0.66 |
| 0.001 | 3 | −0.44 | −0.70 | −0.67 |
| 0.0001 | 4 | −0.73 | −0.73 | −0.73 |

It can be seen that the values of peak current measured in $10^{-4}$ molar (0.1 millimolar) buffer differ from those in 0.1 molar buffer and in the case of phosphate and phthalate buffers the value at somewhat higher buffer concentrations also differ from the values in 0.1 molar buffer.

Example 1

The procedure above was used to test four water-insoluble redox compounds with structures and redox reactions as follows:

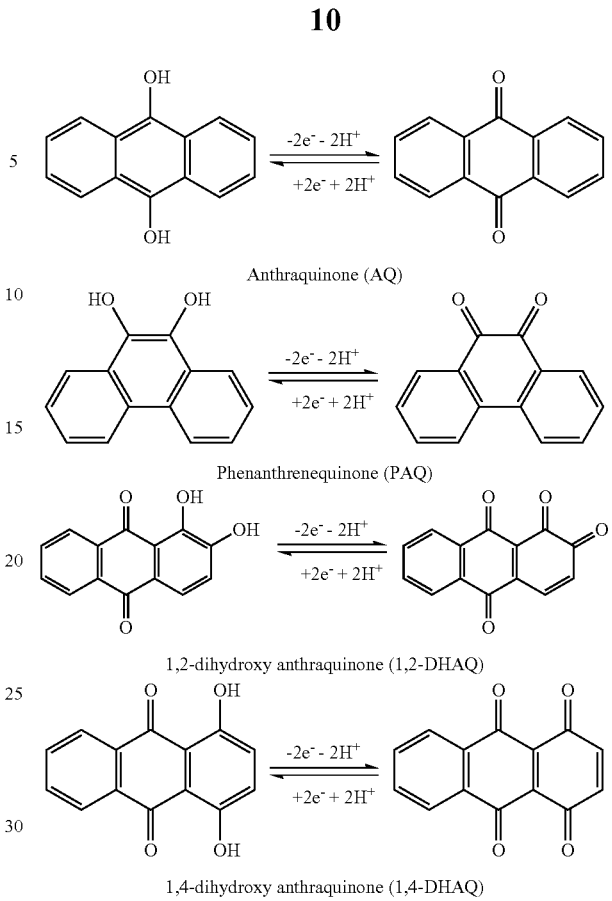

Anthraquinone (AQ)

Phenanthrenequinone (PAQ)

1,2-dihydroxy anthraquinone (1,2-DHAQ)

1,4-dihydroxy anthraquinone (1,4-DHAQ)

When the electrodes with the compounds thereon were used in the above procedure using standard 0.1 molar buffers, straight calibration lines were obtained for each of them. However, when used to measure pH of unbuffered water samples having pH of 8.06 and 7.92 as determined by a glass electrode, the measured oxidative peak voltage corresponded to the following pH values:

| Redox compound | Determined pH for water sample A (actual pH 8.06) | Determined pH for water sample B (actual pH 7.92) |
|---|---|---|
| AQ | 9.73 | 9.32 |
| PAQ | 9.90 | 9.21 |
| 1,4-DHAQ | 8.13 | 7.86 |
| 1,2-DHAQ | 7.90 | 7.84 |

It can be seen that the hydroxy substituted compounds give a measurement of pH which is very close to the value obtained with the glass electrode even though the water samples are not buffered. Without wishing to be bound as to theory, we attribute this to the hydroxy substituents facilitating inter and intra molecular hydrogen bonding for the reduced and oxidized dihydroxyanthraquinone structures within the very short timescale of the proton transfer. This hydrogen bonding reduces the activation energy and facilitates proton transfer to form the unstable intermediates in the oxidation or reduction reaction through electron and proton transfers which are concerted or nearly so.

Figure 4:
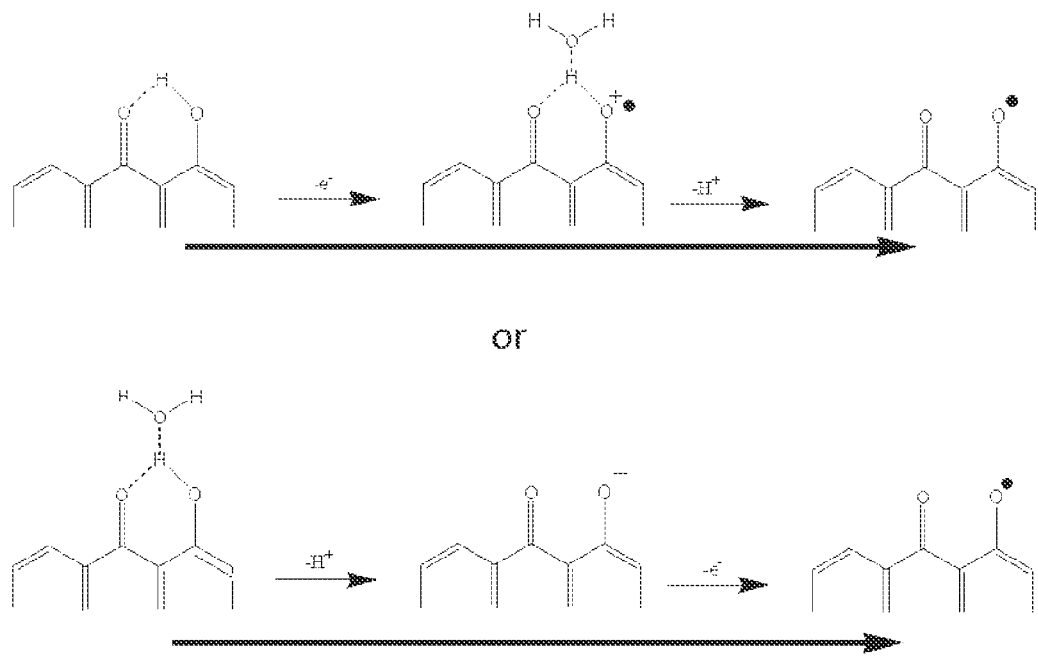
FIG. 4 shows a possible mechanism for the first step of oxidation of 1,4-DHAQ and is described in Example 1.

FIG. 4 shows two possible mechanisms for the first stage of the oxidation of 1,4-DHAQ. In the mechanism at the top of FIG. 4 electron transfer precedes proton transfer. In the other mechanism proton transfer takes place first. It is possible that both mechanisms occur. In both cases an internal hydrogen bond between the hydroxy group and an internal keto oxygen atom forms a ring structure which lowers the activation energy for hydrogen bonding to a water molecule prior to loss of a proton as $H_3O^+$.

Figure 5:
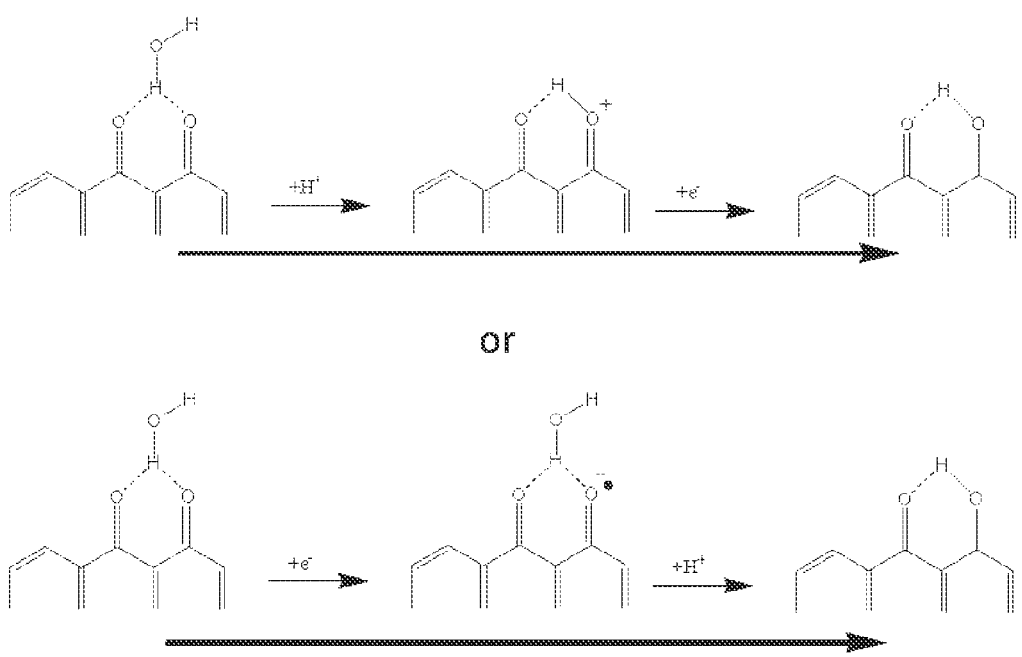
FIG. 5 shows a possible mechanism for the first step of reduction of the oxidised form back to 1,4-DHAQ.

FIG. 5 shows two possible mechanisms for the converse reaction, the corresponding reduction with electron transfer either after or before proton transfer. Again both mechanisms may be occurring. In both mechanisms the adjacent keto oxygen atoms can both hydrogen bond to a water molecule lowering the activation energy for abstraction of a proton from that water molecule.

As a consequence of the enhancement of hydrogen bonding by these structures and lowering of the activation energy for proton transfer, the electron and proton transfers become almost simultaneous i.e. they are concerted or nearly so.

Example 2

The procedure of Example 1 was repeated using unbuffered 0.1 molar potassium chloride solutions as electrolyte. This was done for the two dihydroxyanthraquinones used in Example 1 and also for 1,4-dihydroxynaphthoquinone whose redox conversion to and from a fully oxidised form is

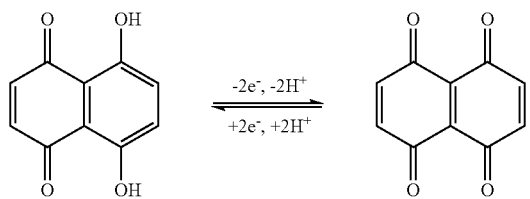 [SMILES: O=C1C=CC(=O)c2c(O)ccc(O)c21 ; O=c1ccc(=O)c2c(=O)ccc(=O)c1=2]

The pH values of the solutions obtained from voltammetry as above and also as measured with a glass electrode are given in the following table:

| Compound | pH determined by voltammetry | pH measured with glass electrode |
| --- | --- | --- |
| 1,4-dihydroxyanthraquinone | 6.52 | 6.35 |
| 1,2-dihydroxyanthraquinone | 6.48 | 6.53 |
| 1,4-dihydroxynapthoquinone | 6.24 | 6.35 |

Example 3

Further evidence that hydrogen bonding takes place and brings about proton transfer was obtained using the following compound, 2,3-dihydro-9,10-dihydroxy-1,4-anthracenedione which undergoes two electron two proton redox reaction as shown

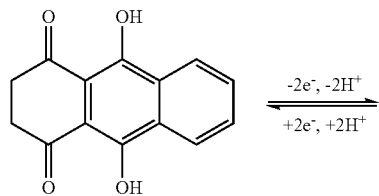

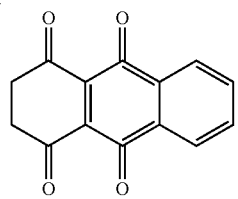

This compound has two keto groups in an aliphatic cyclohexene ring (the left hand ring in the formulae above) which is fused with one ring of a dihydroxy naphthalene structure. This dihydroxy naphthalene portion of the molecule undergoes a two electron two proton redox process. Voltammetry using 0.1 molar buffer solutions showed that voltage at peak current was linearly dependent on pH but measurement in unbuffered salt solution showed an anomalous pH value. The pH value determined by voltammetry was 8.13 whereas the true value measured with a glass electrode was 7.31.

This difference in behaviour compared to 1,4-DHAQ was attributed to the aliphatic ring positioning its keto oxygen atoms out of the plane of the naphthalene rings, so that internal hydrogen bonding was diminished or not possible.

Example 4

Aromatic compounds with two amino substituents can undergo electrochemical oxidation of these groups to an imino form. It would be expected that diamino anthraquinones would form internal hydrogen bonds in a similar manner to dihydroxyanthraquinones.

The procedure of Example 1 was used to test 1,4-DHAQ and also its homologue with an isopropyl group on each nitrogen atom. It was found that the voltammetric responses were complex, apparently because the voltammetry was simultaneously observing redox reaction and protonation at the nitrogen atoms.

The same procedure was then applied to 2,3-dichloro-1,4-diamino-anthraquinone (DCDAAQ). This was found to display useful voltammetry, because the electron-withdrawing chlorine atoms lower the pKa of the amino groups so that protonation is not an interfering effect. The molecule can undergo electrochemical oxidation thus:

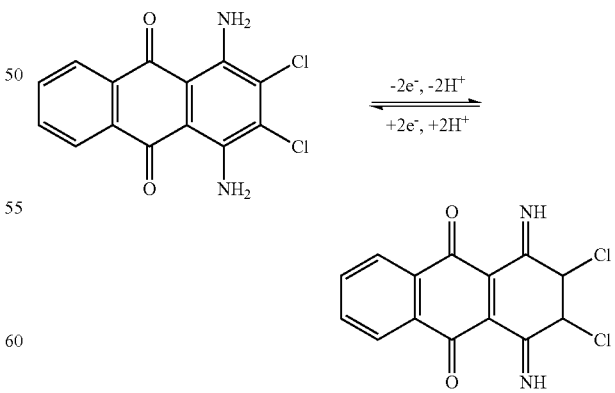

In 0.1 molar buffer solutions the voltages at oxidative peak current were observed to be linearly dependent on pH. In an unbuffered water sample with actual pH by glass electrode of 7.89 the pH determined through voltammetry was 7.89. With another unbuffered water sample with actual pH by glass electrode of 7.13 the pH determined through voltammetry was also 7.13.

Example 5

1,4-dihydroxyanthroquinone can undergo reduction to a compound with four hydroxy groups as well as oxidation to a compound with four keto groups, thus:

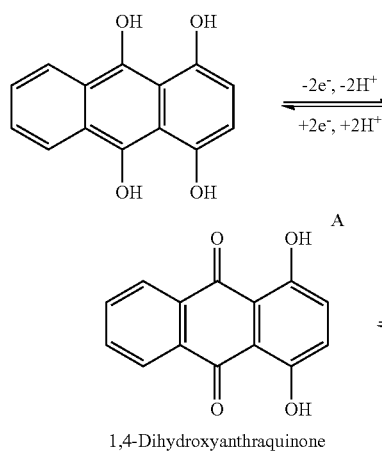

1,4-Dihydroxyanthraquinone

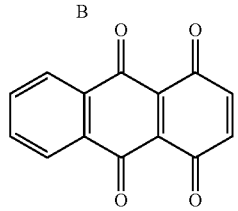

Figure 6:
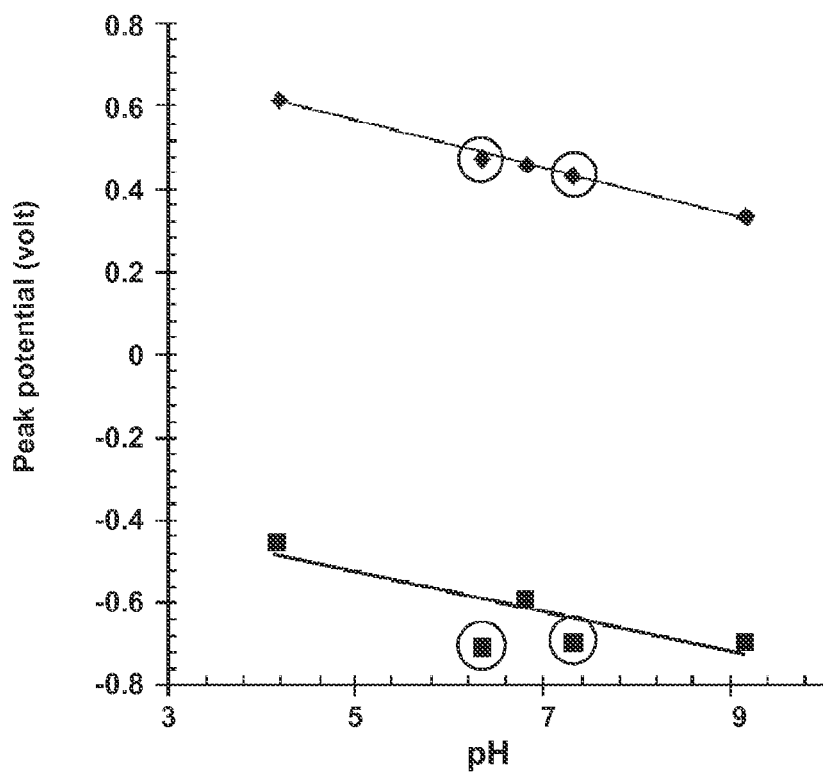
FIG. 6 plots voltages at peak current against pH for both redox reactions of 1,4-DHAQ and is discussed in Example 5.

The two redox reactions have peak currents at different voltages. Voltammetry was carried out using an electrode with this compound deposited on it, using a voltammetric sweep of sufficient width to observe both reactions. The results are shown in FIG. 6. For this figure the voltages at the oxidative peak current and corresponding reductive peak current were averaged. The lower line shown in FIG. 6 connects the results obtained in 0.1 molar buffer solutions for the conversion to and from the fully reduced form with four hydroxy groups which is the reaction A above. The upper line in FIG. 5 connects the results obtained in 0.1 molar buffer solutions for the conversion to and from the fully oxidized form with four keto groups, which is reaction B above.

As can be seen from FIG. 6, both sets of results in 0.1 molar buffer solution showed that voltage at peak current is linearly dependent on pH. For the reaction B, the data points obtained in unbuffered KCl solution and in unbuffered water also lie on this line (as has already been discussed in Examples 1 and 2 above). However, for the reaction on the left the data points in unbuffered KCl and water are somewhat inconsistent with pH as measured with a glass electrode and are spaced away from the lower line in FIG. 6. This was attributed to the free rotation of hydroxyl groups giving less effective hydrogen bonding within the time scale of the redox reaction.

The procedure of this example was repeated with the compounds 1,2-DHAQ, 1,4-DHNQ and DCDAAC mentioned in previous examples. In each case the results were the observation was the same: the data points obtained by voltammetry in unbuffered water samples lay on the upper line (conversion to and from the fully oxidised form) but not on the lower line (conversion to and from the fully reduced form).

Example 6

Figure 7:
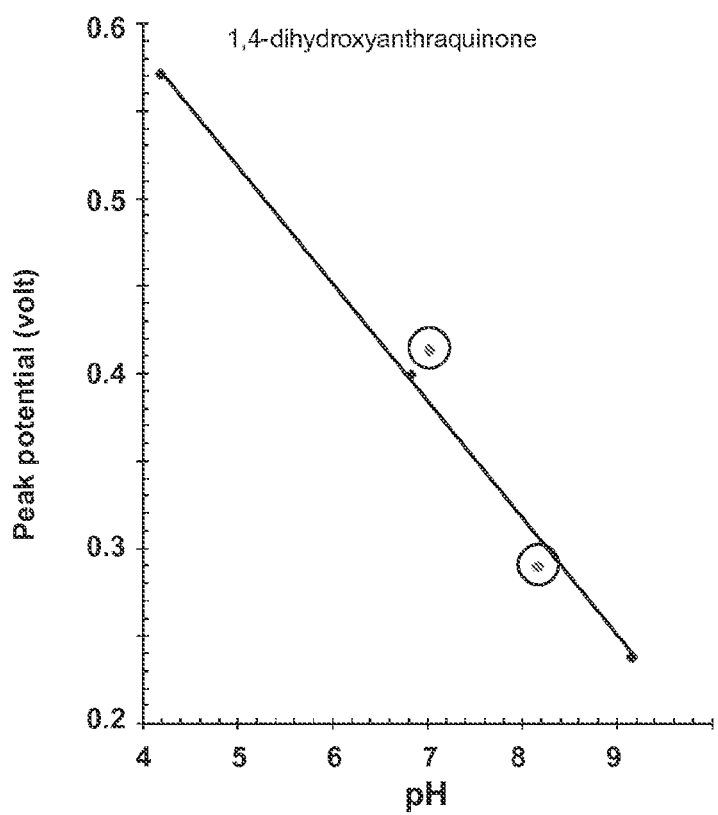
FIG. 7 plots voltages at peak current against pH for conversion of 1,4-DHAQ to and from its fully oxidised form at 60° C., and is discussed in Example 6.

Experiments as in Examples 1 and 2 using 1,4-DHAQ were repeated with the solutions maintained at 60° C. As shown by FIG. 7, the results obtained in 0.1 molar buffer solutions lie on a straight line. The data points in unbuffered water and unbuffered 0.1 molar KCl are shown circled and it can be seen that they lie close to the line.

Example 7

Experiments as in Examples 1 and 2 were carried out using dichloro- and tetrachloro-1,4-benzoquinone, which have the following structures:

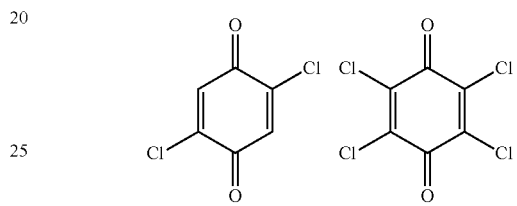

Both of these can undergo reduction to the corresponding hydroquinone. The voltages at oxidative peak and reductive peak currents observed by square wave voltammetry were averaged and plotted against pH as measured with a glass electrode, as shown in FIGS. 8 and 9.

Figure 8:
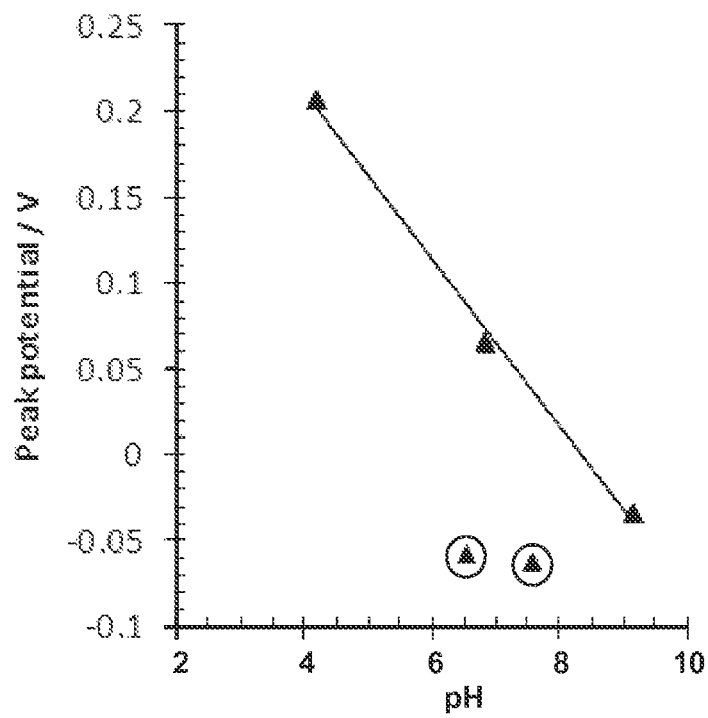
FIG. 8 plots voltages at peak current against pH for conversion of dichloro benzoquinone to and from the corresponding hydroquinone, and is discussed in Example 7.
Figure 9:
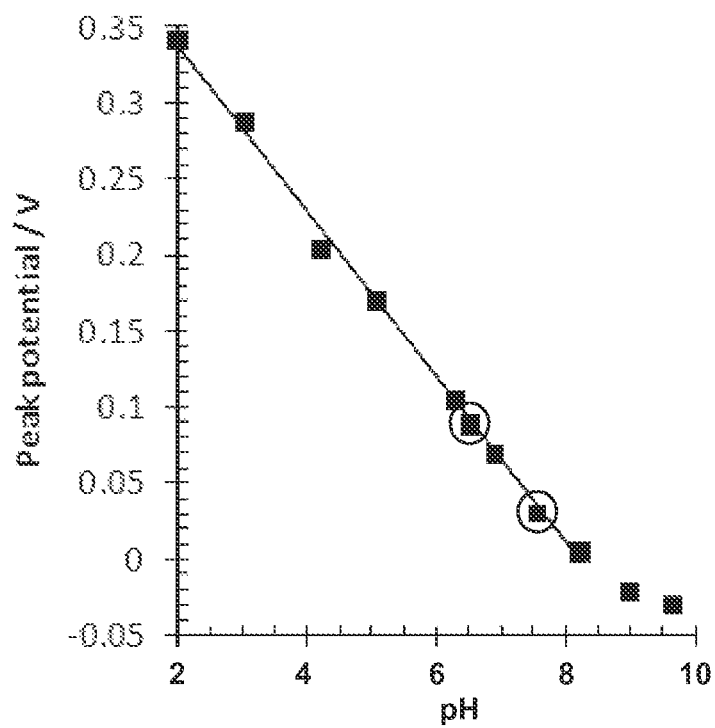
FIG. 9 plots voltages at peak current against pH for conversion of tetrachloro benzoquinone to and from the corresponding hydroquinone, and is also discussed in Example 7.

For both compounds the values obtained in 0.1 molar buffer solutions showed that voltage at peak current is linearly dependent on pH as shown by the straight lines plotted in FIGS. 7 and 8. With the dichloro compound, the results obtained in unbuffered water having a pH of 7.3 measured with a glass electrode and unbuffered KCl solution having a measured pH of 6.3 are anomalous and lie off the straight line. These results are circled in FIG. 8. For the tetrachloro compound, the results obtained in the unbuffered water and KCl solutions (shown circled in FIG. 9) lie on the line.

Without wishing to be limited as to theory, it appears that the halogen substituents are making the molecule more polar and more able to participate in electrostatic interaction with water molecules in the electrolyte. More specifically we attribute this observation to the electron withdrawing halogen substituents having an effect on the surrounding water molecules and making it easier for hydrogen bonding to take place, both in the reductive and the oxidative directions of reaction, thereby reducing the activation energy for the first step of reaction. When there are four halogen substituents on the aromatic ring this effect is sufficiently large that the electron and proton transfers become concerted, or nearly so.

Example 8

Tetra bromo catechol was tested as Example 1. In 0.1 molar buffer solutions the voltages at oxidative peak current were observed to be linearly dependent on pH. Moreover, with the unbuffered water samples as used in Example 1 the pH values obtained were approximately correct. With water sample A with actual pH by glass electrode of 8.06 the pH determined through voltammetry was 8.22. With water sample B with actual pH by glass electrode of 7.92 the pH determined through voltammetry was 8.20.

These good results in unbuffered water were attributed to the electron withdrawing effect of bromine atoms, directly analogous to the result with tetrachloro benzoquinone in the previous example.

The procedure of Example 5 was repeated using the compound 1,2,3,4-tetra fluoro-5,8-dihydroxyanthraquinone (tF-DHAQ) which is a tetra fluoro analogue of 1,4-DHAQ used in Example 5. It can likewise undergo conversion to a reduced form with four hydroxy groups and conversion to an oxidised form with four keto groups as shown:

The three compounds were:

1,2-dihydroxy anthraquinone (1,2-DHAQ) as in Example 1, tetrachloro-1,4-benzoquinone (TCBQ) as in Example 7, and 1,2,3,4-tetra fluoro-5,8-dihydroxyanthraquinone (tF-DHAQ) as in Example 9.

Results for anthraquinone (AQ) in phosphate buffer, as in Comparative Example 2, are also shown here.

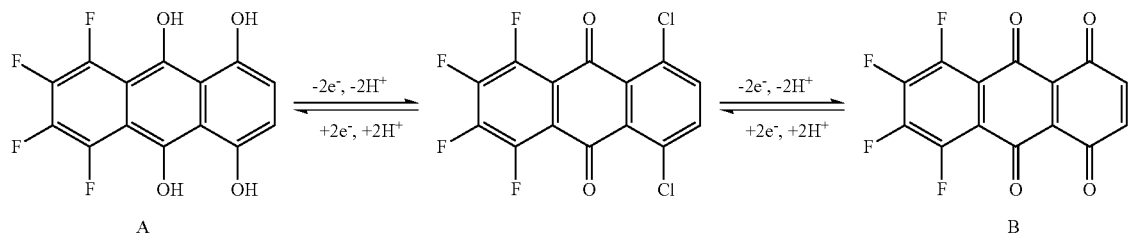

Figure 10:
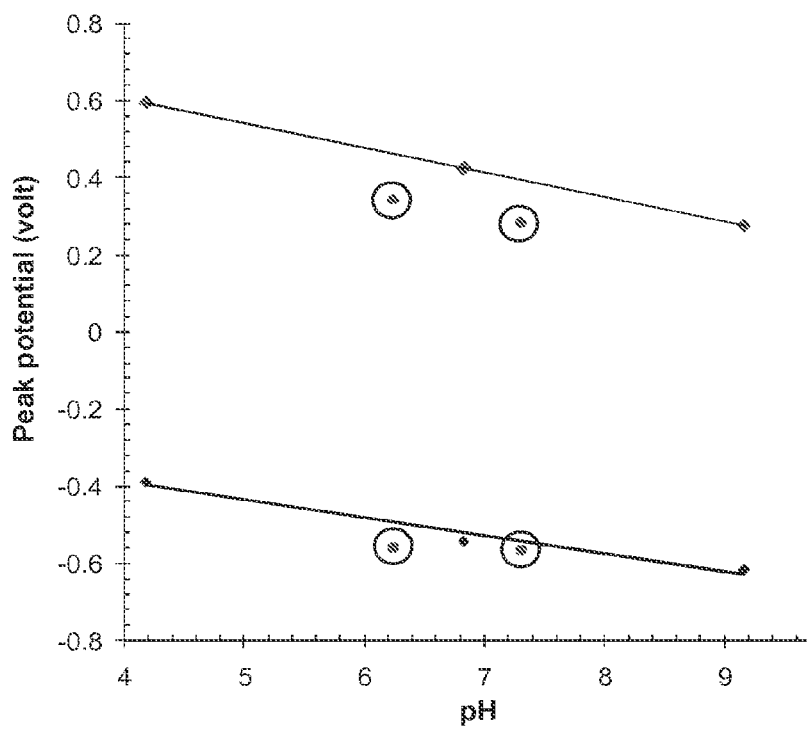
FIG. 10 plots voltages at peak current against pH for both redox reactions of tetrafluoro 1,4-DHAQ and is discussed in Example 9.

The results are shown in FIG. 10. As before in 0.1 molar buffer solutions the data points lie on straight lines indicating that voltage at peak current is linearly dependent on pH. But in contrast to Example 5 the data points (circled) for conversion to and from the fully oxidised form in unbuffered water and KCl solution do not lay on the upper line while the data points for conversion to and from the fully reduced form lie close to the lower line.

Without being bound by theory, we believe that the electron withdrawing effect of the fluorine atoms on the benzyl ring significantly weakens the intramolecular hydrogen bonding of the quinone moiety and the hydroxyl moiety so that oxidation to the fully oxidised diketo compound which is reaction B above and provides the upper line in FIG. 10 is not as facile as in the case of 1,4-dihydroxyanthraquinone. In contrast the electron withdrawing effect of the fluorine atoms facilitates the oxidation and reduction of the first quinone species in reaction A in an analogous manner to that observed with t-chlorobenzoquinone. This is the lower line in FIG. 10.

Each test electrode was electrically connected to the ferrocene reference electrode and square wave voltammetry was carried out in solutions containing phosphate buffer at a variety of concentrations ranging from 0.0001 molar to 0.1 molar, together with potassium chloride where required to make up the electrolyte concentration to 0.1 molar. In each case the phosphate buffer contained $Na_2HPO_4$ and $KH_2PO_4$ in proportions to buffer the solution to pH7.0 as determined using a glass electrode. The voltages corresponding to peak oxidative current were measured, and the results are set out in the following table.

| Concentration of phosphate ion | Voltage at peak oxidative current | | | |
|---|---|---|---|---|
| | Anthraquinone | Dihydroxy-anthraquinone | Tetrachloro-benzoquinone | Tetrafluorodihydroxy-anthraquinone |
| 0.1M | −0.51 | 0.38 | 0.10 | 0.45 |
| 0.01M | −0.51 | 0.38 | 0.09 | 0.44 |
| 0.005M | −0.53 | 0.38 | 0.10 | 0.44 |
| 0.003M | −0.55 | 0.37 | 0.10 | 0.44 |
| 0.001M | −0.70 | 0.38 | 0.10 | 0.46 |
| 0.0001M | −0.73 | 0.39 | 0.10 | 0.43 |

Example 10

The above experimental procedure was used to examine the behaviour of three of the above compounds in varying concentrations of phosphate buffer. As in previous examples test electrodes were prepared using the procedure described above in which a redox compound is deposited onto a glassy carbon electrode by evaporation from a solution of dichloromethane, and a pH insensitive reference electrode was prepared in the same way, using ferrocene as the redox compound.

Figure 11:
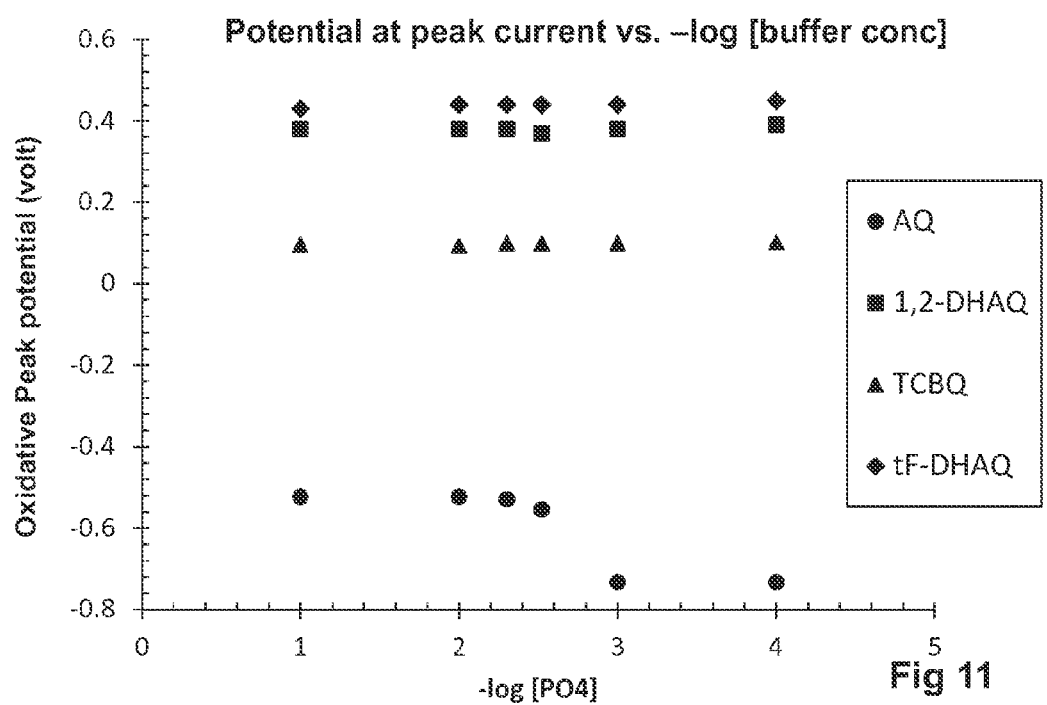
FIG. 11 shows voltages at peak current obtained in Example 10 plotted against minus log buffer concentration.

As can be seen from these results, the substituted quinones gave results in $10^{-4}$ molar buffer which were consistent with results in standard 0.1 molar buffer. These results are shown in graphical form in FIG. 11 where the concentration of phosphate ions is shown on a negative logarithmic scale so that the low concentrations are towards the right of the graph.

The oxidation potentials of some of the compounds mentioned in the previous examples were determined in 0.1 molar buffer solutions having a pH of 1.7. The oxidation potential of anthraquinone was also measured under the same conditions. The potentials were measured relative to a standard calomel electrode and the results obtained were:

| | |
|---|---|
| 1,2-dihydroxyanthraquinone | 0.68 volt |
| 1,4-dihydroxyanthraquinone | 0.88 volt |
| tetrabromocatechol | 0.52 volt |
| anthraquinone | −0.20 volt |

In some embodiments, a redox active compound which is sensitive to the analyte concentration/pH may be used jointly with a redox active compound which is substantially insensitive to the concentration of analyte/pH. This species which is independent of analyte concentration may function as a reference and the potential of the sensitive compound may be determined relative to the potential of the compound which is insensitive to the concentration of analyte/pH. Possible reference molecules, insensitive to hydrogen ion concentration are $K_5Mo(CN)_8$ and molecules containing ferrocene such as potassium t-butylferrocene sulfonate.

Figure 12:
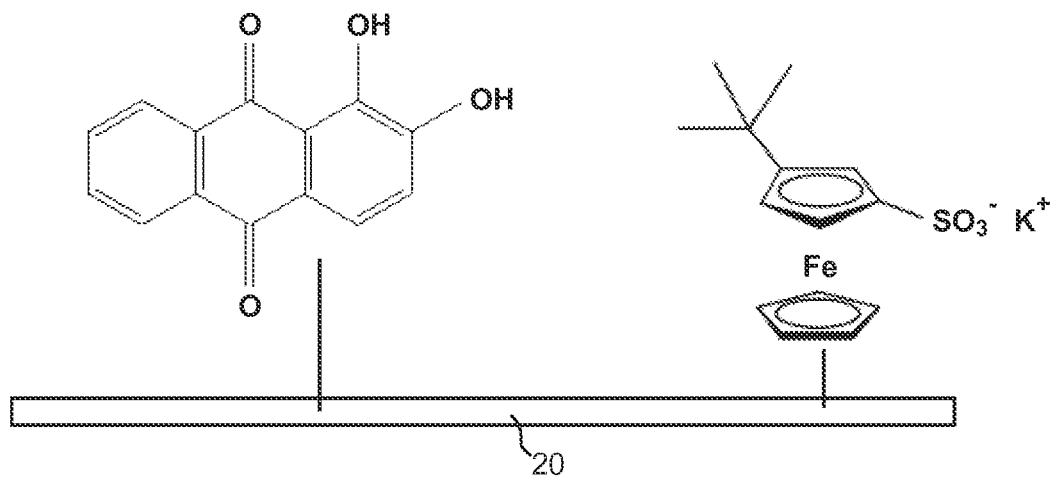
FIG. 12 diagrammatically illustrates the surface structure of a measuring electrode with an internal reference electrode.

When a redox active compound which is sensitive to the analyte concentration/pH is immobilized on an electrode, a reference redox active compound which is substantially insensitive to the concentration of analyte/pH may be immobilized on the same electrode or on another electrode. FIG. 12 diagrammatically illustrates a pH-sensitive compound, 1,2-dihydroxyanthraquinone, and a pH-insensitive compound, t-butylferrocene sulfonate, immobilized on the same conductive electrode substrate 20. Immobilization on separate electrodes would avoid any risk that deposition of a second compound on an electrode overlies and hides one already deposited and so ensure that both redox active compounds are accessible to the surrounding solution. The two electrodes may then be connected together so that only a single voltammetric sweep is required.

In the experimental examples above, the redox active compound was immobilized on the surface of a glassy carbon electrode by evaporation of a solution or suspension, thus associating a redox active compound with a conductive electrode material, so that the redox active compound is held close to conductive material. Other forms of carbon may be used for electrodes. The most common forms of conducting carbon used in electrode manufacture are glassy carbon, carbon fibres, carbon black, various forms of graphite, carbon paste and carbon epoxy. One further form of carbon, which has seen a large expansion in its use in the field of electrochemistry since its discovery in 1991 is the carbon nanotube (CNT). The structure of CNTs approximates to rolled-up sheets of graphite and can be formed as either single or multi-walled tubes. Single-walled carbon nanotubes (SWCNTs) constitute a single, hollow graphite tube. Multi-walled carbon nanotubes (MWCNTs) on the other hand consist of several concentric tubes fitted one inside the other. Untreated multi-walled nanotubes can be purchased from commercial vendors, for example from Nano-Lab Inc of Brighton, Mass., USA in 95% purity with a diameter of 30+/−15 nm and a length of 5-20 μm.

Another possible way of immobilizing redox active compounds onto an electrode is by packing a mixture of the compounds and carbon powder into a recessed cavity in an electrode without using a binding substance. The carbon powder could be mixed with the pH-sensitive redox active compound and any reference compound and ground finely with a mortar and pestle. Then the empty recess might be filled with the powder mix which would be mechanically compacted. The resulting void in the recess would then be refilled and compacted again. This would be repeated several times until the recess is full. The material would be pressed such that the particles are packed into a dense matrix.

The above method results in physical attachment of redox active compound(s) to an electrode. A further possibility is chemical attachment of redox compound(s) to carbon. This is referred to as "derivitising" the carbon. A possible method for derivitising carbon is the chemical reduction of aryldiazonium salts with hypophosphorous acid.

An example of preparation process for derivatised MWCNT involves the following steps: first 50 mg of MWCNTs are stirred into 10 $cm^3$ of a diazonium salt of the redox active compound and 50 $cm^3$ of hypophosphorous acid ($H_3PO_2$, 50% w/w in water) is added. Next the solution is allowed to stand at 5° C. for 30 minutes with gentle stirring. After this the solution is filtered by water suction in order to remove any unreacted species from the MWCNT surface. Further washing with deionized water is carried out to remove any excess acid and finally with acetonitrile to remove any unreacted diazonium salt from the mixture. The derivatised MWCNTs are then air-dried by placing them inside a fume hood for a period of 12 hours after which they are stored in an airtight container prior to use.

The reduction of diazonium salts using hypophosphorous acid is a versatile technique for the derivatization of bulk graphite powder and MWCNTs. Derivitisation may also be carried out using a very strong base to convert a precursor to a reactive carbene which then forms covalent bonds to a carbon surface, as described in WO2010/106404.

In further embodiments, a redox active compound which is sensitive to the analyte concentration/pH may be screen printed onto a substrate which may be an insulating material. A second redox active compound that is insensitive to analyte/pH and acts as a reference may be screen printed onto the same or another substrate. The redox active species, whether sensitive or insensitive to analyte/pH, may be combined with a binding material, which may be a conductive binding material such as a graphite-containing ink, and then screen printed onto the electrode. In these embodiments, a simple screen printed substrate may provide a pH sensor that does not require a buffer. An external reference electrode may possibly be used with the screen-printed electrode. One possible external reference is a silver/silver-chloride electrode. A screen-printed electrode may possibly carry such an external reference electrode on a portion of an insulating substrate. A pH sensitive and/or pH insensitive redox species may also be applied to the working electrode by an inkjet-type process in combination with a binder, such as ink.

Some embodiments provide an electrochemical sensor for measuring an analyte and/or pH, comprising one or more redox active compounds sensitive to the analyte/pH and coupled with an electrode to provide for detection/measurement of the analyte/pH, wherein the electrode is at least partially covered by a polymer coating. A screen-printed electrode may possibly be covered with a film or coating, such as a polymer film or coating. The polymer film or coating may, among other things, make the electrode more robust, prevent external adverse effects of the redox species, and allow for sterilization of the electrode without affecting the functionality of the electrode.

Some embodiments of electrochemical sensor include a temperature probe for measuring a temperature of the fluid, wherein the temperature measurement may be used to calibrate the electrochemical sensor.

A sensor as disclosed hereincould be incorporated into a wide variety of tools and equipment. Possibilities include use in tools which are located permanently downhole, use in tools which are conveyed downhole, for instance at the head of coiled tubing or by drillpipe or on a wireline, use in underground, undersea or surface pipeline equipment to monitor liquid flowing in the pipeline, and use in a wide variety of process plant at the Earth's surface, including use in water treatment.

Figure 13:
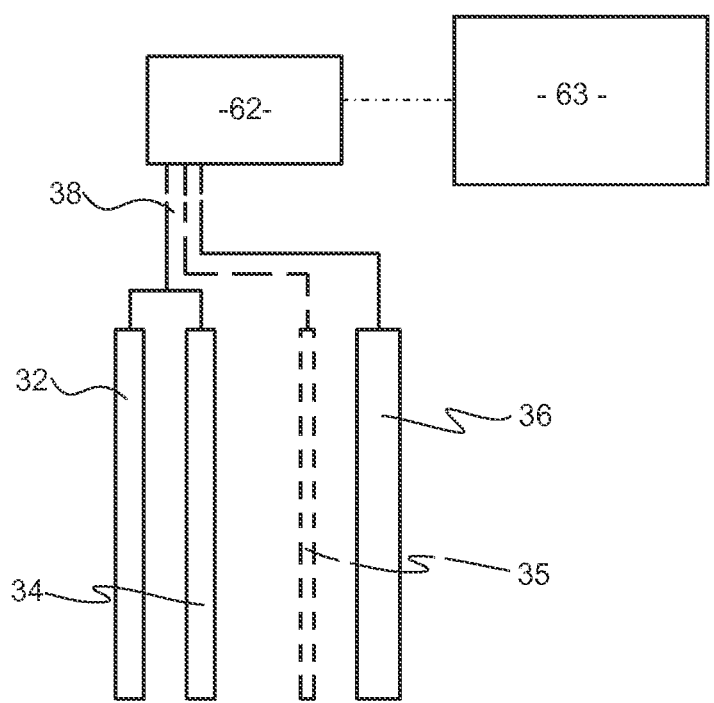
FIG. 13 is a diagrammatic illustration of the parts of a sensor.

FIG. 13 diagrammatically illustrates component parts which may be used in a sensor. There is a working electrode 32 comprising a conductive material with 1,4-DHAQ or other redox active compound as described above immobilized on its surface, and a second electrode 34 which is also a conductive material but which has ferrocene immobilized on its surface and which serves as a voltage reference, and a counter electrode 36. All the electrodes are connected as indicated at 38 to a potentiostat 62 or other control unit which provides electric power and measurement. This arrangement avoids a need for a standard reference electrode such as a standard calomel electrode. However, another possibility would be to provide such a standard electrode, as shown by broken lines at 35 and possibly dispense with the ferrocene electrode 34. The various electrodes are immersed in or otherwise exposed to fluid whose pH is to be measured.

Measuring apparatus may comprise both a sensor and a control unit providing both electrical power and measurement. A control unit such as 62 may comprise a power supply, voltage supply, potentiostat and/or the like for applying an electrical potential to the working electrode 32 and a detector, such as a voltmeter, a potentiometer, ammeter, resistometer or a circuit for measuring voltage and/or current and converting to a digital output, for measuring a potential between the working electrode 32 and the counter electrode 36 and/or the reference electrode 34 or 35 and for measuring a current flowing between the working electrode 32 and the counter electrode 36 (where the current flow will change as a result of the oxidation/reduction of a redox species). The control unit may in particular be a potentiostat. Suitable potentiostats are available from Eco Chemie BV, Utrecht, Netherlands.

A control unit 62 which is a potentiostat may sweep a voltage difference across the electrodes and carry out voltammetry so that, for example, linear sweep voltammetry, cyclic voltammetry, or square wave voltammetry may be used to obtain measurements of the analyte using the electrochemical sensor. The control unit 62 may include signal processing electronics.

A control unit 62 may be connected to a computer 63 which receives current and/or voltage data from the sensor. This data may be the raw data of applied voltage and the current flowing at that voltage, or may be processed data which is the voltage at peak current. A control unit 62, such as a potentiostat may itself be controlled by a programmable computer 63 giving a command to start a voltage sweep and possibly the computer will command parameters of the sweep such as its range of applied voltage and the rate of change of applied voltage.

Figure 14:
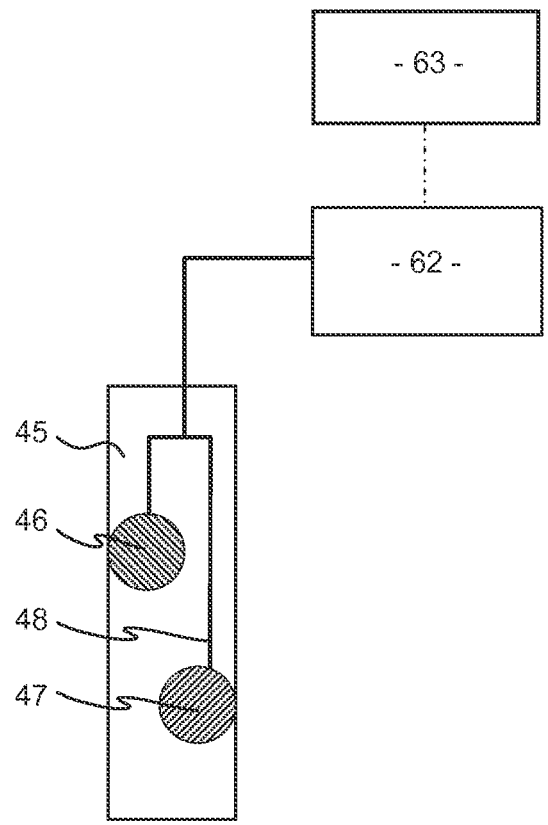
FIG. 14 shows another electrode construction.

FIG. 14 shows a possible variation. A conductive paste containing a pH sensitive redox compound is printed on one area 46 of an insulating substrate 45 to provide an electrode 32. A second conductive paste containing a pH insensitive ferrocene compound is printed on an area 47 as a reference electrode. Both areas 46,47 are connected together by conductive tracks 48 on the substrate which are connected as shown to a control unit 62 which may in turn be connected to a programmable computer 63 receiving data from the sensor.

Figure 15:
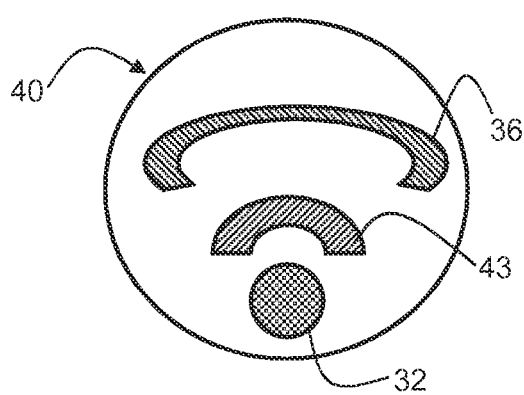
FIG. 15 illustrates the geometrical surface layout of the surface of a sensor.

FIG. 15 shows a possible geometric configuration or layout for the surface 40 of a sensor which is exposed to the fluid to be tested, which may, merely by way of example be a wellbore fluid. The surface includes a disk shaped working electrode 32, a second electrode 43, which may be a ferrocene electrode or an external reference electrode such as a silver/silver chloride electrode, and a counter electrode 36.

Figure 16:
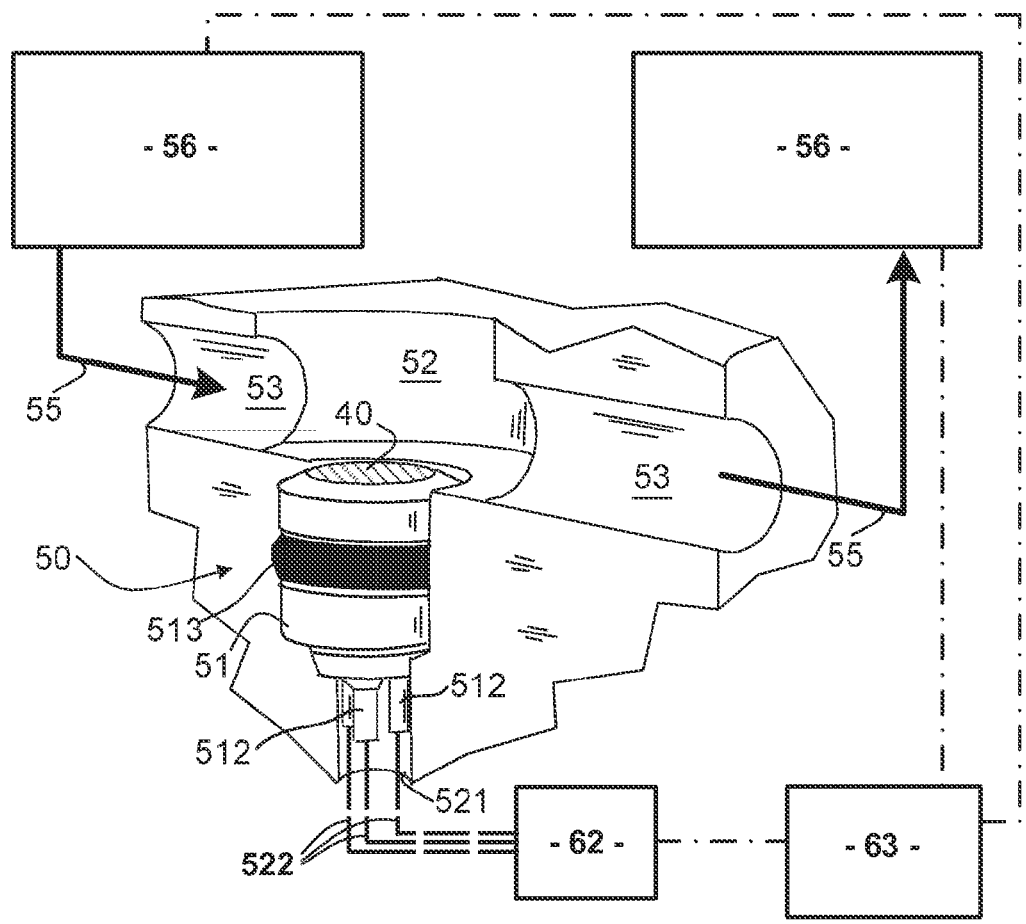
FIG. 16 is a perspective view, partially cut-away, of a flow line fitted with an electrochemical sensor incorporating the surface of FIG. 15.

A schematic of a microsensor 50 incorporating such a surface is shown in FIG. 16. The surface 40 of a sensor 50 is exposed to liquid in a channel 53 which may be part of a flow line for a material flowing into, within or out from equipment which is a process plant for an aqueous liquid. Flow is indicated by arrows 55. The body 51 of the sensor 50 is fixed into the end section of an opening 52. The body carries the electrode surface 40 and has contacts 512 located in a small channel 521 at the bottom of the opening 52. A sealing ring 513 protects the contact points and electronics from the fluid to be tested that passes under operation conditions through the channel 53. Other parts of the process plant are indicated schematically by boxes 56. The contacts 512 of the sensor are electrically connected by cables 522 to a potentiostat 62 for voltage supply and current measurement. This potentiostat 62 receives operating commands from a computer 63 and sends data, consisting of the applied potential and observed current to the computer 63. The computer is also connected, as shown by chain dotted lines, to other parts of the process plant 56 and controls its operation, such as by operating valves and heaters (not shown separately) within the plant 56.

Figure 17:
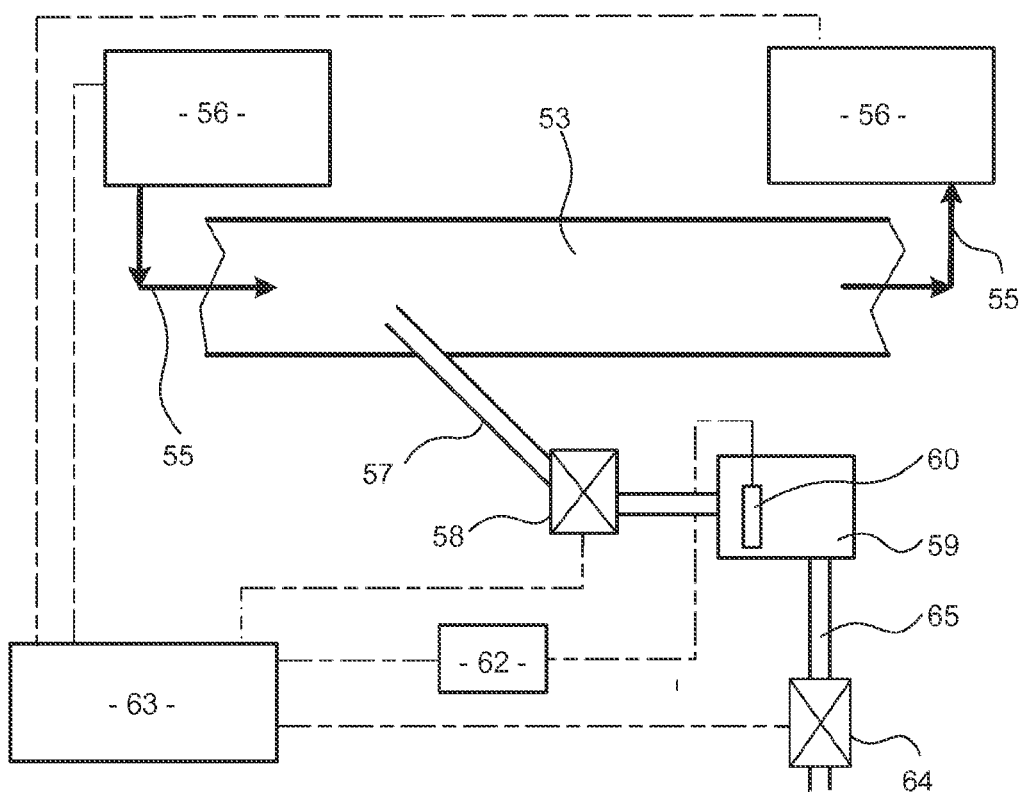
FIG. 17 is a diagrammatic view of a flow line with means for taking samples and measuring the pH of the samples.

FIG. 17 shows diagrammatically an arrangement for periodically taking samples and determining pH. An aqueous liquid to be sampled flows in line 53 as shown by arrows 55. A sampling tube 57 projects into the flow path. When a sample is to be taken, valve 58 is opened, allowing liquid to flow through the tube 57 into chamber 59. This chamber 59 has a sensor 60 within it for measuring the pH of fluid within the chamber 59. This sensor may be of the type shown in FIG. 13 or the type shown in FIG. 14. It is connected to a potentiostat 62. The line 53 is part of equipment 56 for processing water or other aqueous liquid. This plant is controlled by a programmable computer 63 which also operates the valve 58 when required and a further valve 64 for draining the chamber 59 through tube 65. Connections to the computer are shown by chain dotted lines. The computer may be programmed to maintain stable pH, so that pH measurement forms part of a control system, or it may monitor pH and alert a human supervisor if pH goes out of an acceptable range. The latter might be done as a check on incoming water or other aqueous feedstock, for instance.

Figure 18:
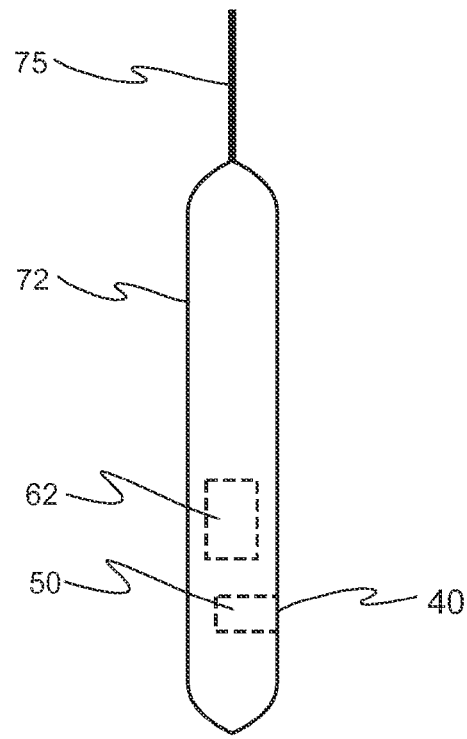
FIG. 18 is a diagrammatic illustration of a cable-suspended tool for testing water.

An application of an embodiment of the present invention may be in the monitoring of underground bodies of water for the purposes of resource management. From monitoring wells drilled into the aquifers, one or more sensors, may be deployed on a cable from the surface—either for short duration (as part of a logging operation) or longer term (as part of a monitoring application). FIG. 18 illustrates a tool for investigating subterranean water. This tool has a cylindrical body 72 which is suspended from a cable 75. A sensor unit similar to the body 51 shown in FIG. 16 is accommodated within the body 72 so that its surface 40 is exposed to the subterranean water. The tool also encloses also encloses a unit 62 which is a potentiostat for supplying voltage to the electrodes of the sensor unit 51, measuring the current which flows and transmitting the results to the surface.

The deployment of such a pH sensor within producing wells on a cable may provide information on produced water quality. Also, the pH sensor may be deployed in injection wells, e.g. when water is injected into an aquifer for later retrieval, where pH may be used to monitor the quality of the water being injected or retrieved.

FIG. 15 shows a formation testing apparatus 810 held on a wireline 812 within a wellbore 814. The apparatus 810 is a well-known modular dynamic tester (MDT, Trade Mark of Schlumberger) as described in the co-owned U.S. Pat. No. 3,859,851 to Urbanosky, U.S. Pat. No. 3,780,575 to Urbanosky and U.S. Pat. No. 4,994,671 to Safinya et al., with this known tester being modified by introduction of an electrochemical analyzing sensor 816 substantially similar to sensor 50 of FIG. 16 The modular dynamics tester comprises body 820 approximately 30 m long and containing a main flowline bus or conduit 822. The analysing tool 816 communicates with the flowline 822 via opening 817. In addition to the novel sensor system 816, the testing apparatus comprises an optical fluid analyser 830 within the lower part of the flowline 822. The flow through the flowline 822 is driven by means of a pump 832 located towards the upper end of the flowline 822. Hydraulic arms 834 and counterarms 835 are attached external to the body 820 and carry a sample probe tip 836 for sampling fluid. The base of the probing tip 836 is isolated from the wellbore 814 by an o-ring 840, or other sealing devices, e.g., packers.

Before completion of a well, the modular dynamics tester is lowered into the well on the wireline 812. After reaching a target depth, i.e., the layer 842 of the formation which is to be sampled, the hydraulic arms 834 are extended to engage the sample probe tip 836 with the formation. The o-ring 840 at the base of the sample probe 836 forms a seal between the side of the wellbore 844 and the formation 842 into which the probe 836 is inserted and prevents the sample probe 136 from acquiring fluid directly from the borehole 814.

Once the sample probe 836 is inserted into the formation 842, an electrical signal is passed down the wireline 812 from the surface so as to start the pump 832 and the sensor systems 816 and 830 to begin sampling of a sample of fluid from the formation 842. The electrochemical sensor 816 can then measure the pH of the formation effluent.

While the preceding uses of the electrochemical sensor are in the hydrocarbon and water industries, embodiments of the present invention may provide an electrochemical sensor for measuring pH in a wide range of industries, including food processing, pharmaceutical, medical, water management and treatment, biochemistry, research laboratories and/or the like.

A screen-printed electrode may be used in combination with a hand-held potentiostat to measure pH. Merely by way of example, screen printed carbon electrodes may be fabricated using stencil designs to delineate the components of the electrode. Constituents of the electrode may possibly be sequentially deposited onto the electrode. By way of example, carbon/graphite may be deposited onto a reference electrode comprising a substrate, which may comprise a plastic, polyester and/or the like. A reference electrode, such as silver/silver-chloride and or the like may then be deposited as a paste onto the electrode. The redox species for the electrode may be mixed within a carbon-graphite ink and deposited on the electrode. In certain aspects, dielectric compounds may be used as binders for the screen-printed working electrode. Finally, the electrode may be dried, possibly using an oven. In some embodiments, a polymer coating may be applied on top of the electrode.

Figure 20:
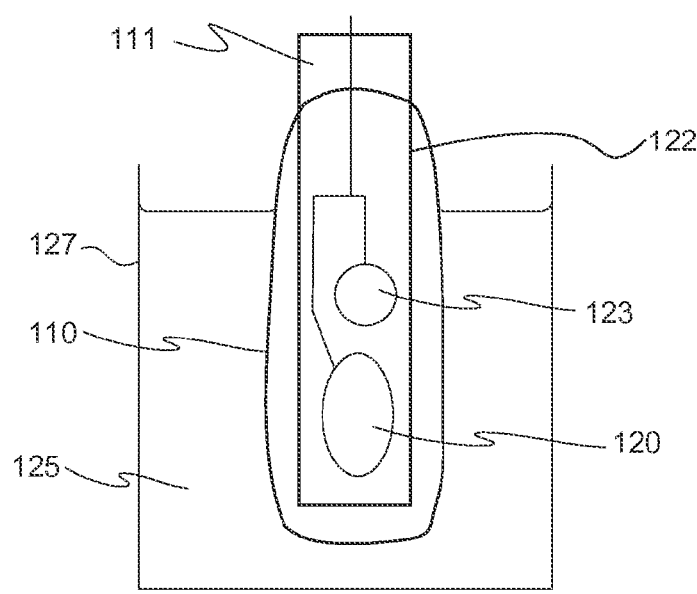
FIG. 20 illustrates a working electrode covered at least in part by a polymer layer.
Figure 19:
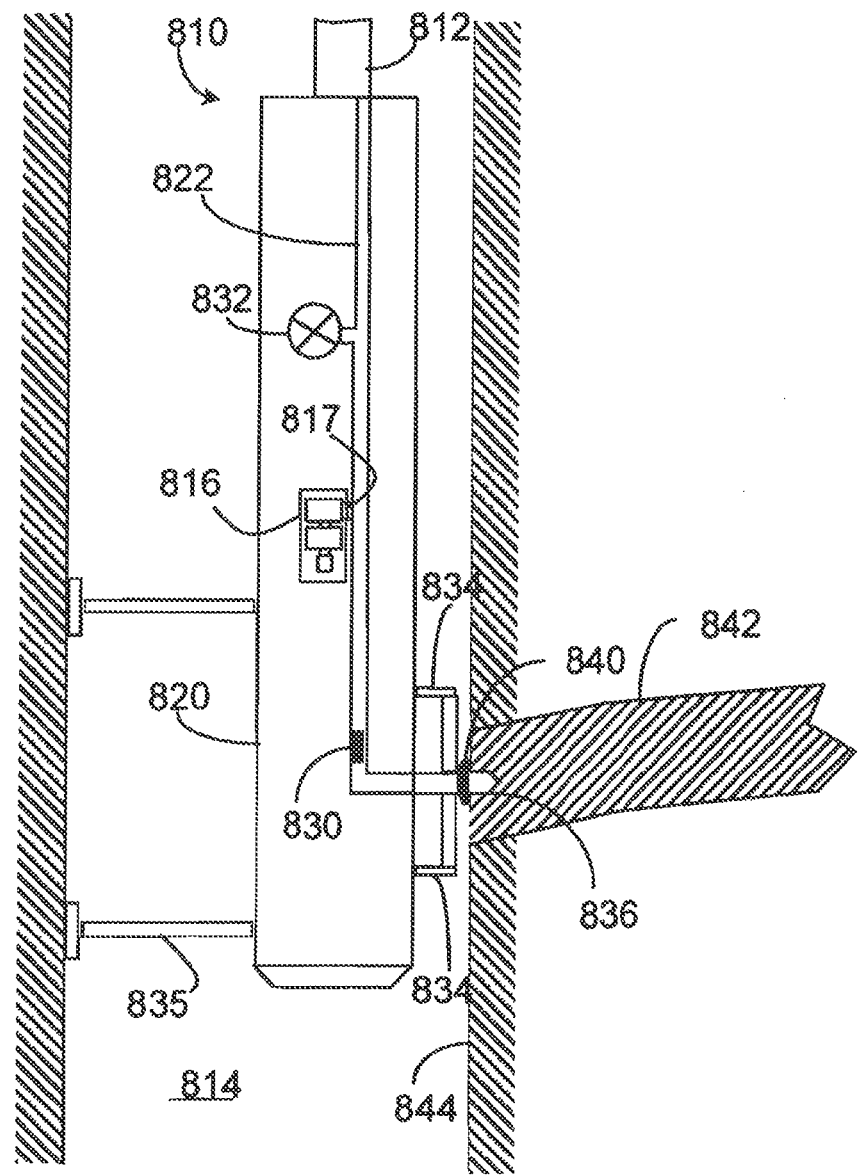
FIG. 19 illustrates an example of an electrochemical sensor as part of a wireline formation testing apparatus in a wellbore.

A polymer coating may prevent diffusion of a redox species from the working electrode, but still allow for interactions between an analyte and one or more of the redox species disposed on the working electrode. FIG. 20 is a schematic representation of a working electrode 111 with polymer coating 110 over a lower portion of the working electrode. This working electrode 111 comprises a redox species 120 sensitive to pH of an aqueous liquid 125 in contact with the electrode 1110 and a reference redox species 123 which is insensitive to pH of liquid 125. These are connected by conductive tracks on the substrate of the electrode 111.

This electrode 111 could be used in combination with a hand-held potentiostat, for instance to measure pH of a sample in a beaker 127 as shown in FIG. 20. However, an electrode with a polymer coating such as electrode 111 could also be incorporated into apparatus for automated sampling, such as electrode 60 shown in FIG. 17 or be used in other equipment for processing aqueous liquid where a programmable computer receives measurement data from the electrode 111.

A polymer coating 110 may serve to prevent leaching, diffusion and/or the like of the redox species 120, 123 into the surrounding fluid. This may be important where it is not desirable to contaminate the fluid, for example the fluid may be water in a water treatment process, a batch of a pharmaceutical process, a food substance or the like. In other aspects, the electrochemical sensor/working electrode may be subject to human contact in use and it may be desirable to prevent such contact with the redox species. Alternatively or in addition, the application of the polymer coating 110 to the working electrode 111 may serve to anchor the redox species 120, 123 to the working electrode 111. As such, methods of fabrication of the working electrode may be used wherein the redox species are not chemically coupled to the working electrode 111. At the same time, the polymer coating 110 should allow the fluid 125 to permeate, diffuse or otherwise come into contact with the redox species 120 and 123 on the working electrode 111. Merely by way of example the polymer coating 110 may comprise a polysulphone polymer or a polystyrene polymer. Other polymers may be used provided the polymers do not interfere with the operation of the sensor.

Methods to deposit the polymer in a generally uniform layer over the working electrode 111 include spin coating onto the working electrode 111, dip coating onto the working electrode 111 and application using solvent evaporation onto the working electrode 111. A screen printing process may possibly be used to apply the sensitive redox species 120, the insensitive redox species 123 and/or the polymer coating 110 to the working electrode 111.

The invention claimed is:

1. A method of measuring the pH of an aqueous liquid, comprising exposing the aqueous liquid comprising buffer at a concentration of 0.01 molar or less to an electrochemical sensor comprising an electrode with a redox active compound immobilized to the electrode with at least one functional group convertible electrochemically between reduced and oxidized forms upon transfer of at least one proton between the compound and surrounding aqueous phase, wherein the reduced form of the redox active compound incorporates a partial structure,

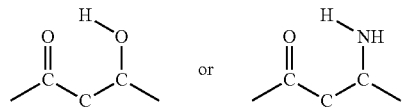

wherein the oxidized form of the redox active compound incorporates a partial structure,

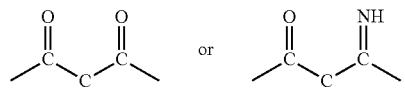

where the carbon atoms are joined by conjugated bonds in both the reduced form and the oxidized form of the redox active compound, wherein the compound has at least one keto group, which is positioned to participate in internal hydrogen bonding with the at least one functional group in its reduced form and increases the reaction rate of proton transfer by reducing the activation energy for transfer of a proton and/or promoting hydrogen bonding at a said functional group,

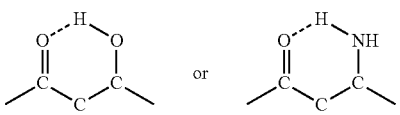

and
observing the redox reaction at the electrochemical sensor.

2. A method according to claim 1 comprising applying variable potential to the electrode with the redox-active compound immobilized thereon; and determining the applied potential at a maximum current for redox reaction of the compound.

3. A method according to claim 1 wherein the aqueous liquid is unbuffered water.

4. A method according to claim 1 wherein the aqueous liquid contains buffer at a concentration of at least $10^{-6}$ molar.

5. A method according to claim 1 wherein the carbon atoms of the redox active organic compound, which are joined by conjugated bonds, are provided by at least two fused aromatic rings.

6. A method according to claim 5 wherein said compound comprises at least two fused aromatic rings, which has two keto substituents on a first aromatic ring and two oxygen-containing functional group convertible between hydroxyl and keto forms on a second aromatic ring fused with the first said ring.

7. A method according to claim 5, wherein the compound comprises at least two fused aromatic rings with two keto substituents on a first aromatic ring and at least two nitrogen containing functional groups, convertible between reduced and oxidized forms, on a second aromatic ring fused with the first said ring, and the compound further having electron withdrawing substituents reducing the basicity of the nitrogen-containing functional group.

8. A method according to claim 5 wherein said redox active organic compound further comprises an electron withdrawing group.

9. A method according to claim 1, wherein the redox active compound is selected from 1,4-diamino-2,3-dihalo-naphthoquinone, 2-acetylbenzoquinone, 2,3-diacetylbenzoquinone, 1,2-dihydroxynaphthoquinone, 1,4-dihydroxynaphthoquinone and homologues and analogues of these compounds which have additional substituents or have additional rings fused with the benzoquinone or naphthoquinone rings, and wherein the keto groups of the benzoquinone or napthoquinone may be in ortho or para positions relative to each other.

10. A sensor according to claim 1 comprising a plurality of electrodes with the redox active compound immobilized on one of the electrodes.

11. A method according to claim 1 wherein the sensor further comprises a second redox active compound as a reference, immobilized to the same or another electrode, the oxidation and reduction of the second redox active compound being substantially insensitive to pH.

* * * * *